United States Patent
Hu et al.

(10) Patent No.: US 10,196,385 B2
(45) Date of Patent: Feb. 5, 2019

(54) TETRAHYDROPYRANYL BENZAMIDE DERIVATIVES

(71) Applicant: Eli Lilly and Company, Indianapolis, IN (US)

(72) Inventors: Zhi Long Hu, Shanghai (CN); Lian Zhu Liu, Shanghai (CN); Tianwei Ma, Shanghai (CN); Haizhen Zhang, Shanghai (CN); Jingye Zhou, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 351 days.

(21) Appl. No.: 15/118,295

(22) PCT Filed: Feb. 19, 2016

(86) PCT No.: PCT/CN2016/074083
§ 371 (c)(1),
(2) Date: Aug. 11, 2016

(87) PCT Pub. No.: WO2016/138821
PCT Pub. Date: Sep. 9, 2016

(65) Prior Publication Data
US 2018/0194755 A1    Jul. 12, 2018

(30) Foreign Application Priority Data
Mar. 3, 2015 (WO) ................ PCT/CN2015/073563

(51) Int. Cl.
| C07D 405/14 | (2006.01) |
| C07D 413/14 | (2006.01) |
| C07D 471/04 | (2006.01) |
| C07D 498/04 | (2006.01) |
| A61P 3/10 | (2006.01) |

(52) U.S. Cl.
CPC .............. *C07D 405/14* (2013.01); *A61P 3/10* (2018.01); *C07D 413/14* (2013.01); *C07D 471/04* (2013.01); *C07D 498/04* (2013.01); *A61K 2121/00* (2013.01)

(58) Field of Classification Search
None
See application file for complete search history.

(56) References Cited

U.S. PATENT DOCUMENTS

2012/0004227 A1    1/2012   Yoshida et al.

FOREIGN PATENT DOCUMENTS

| WO | 2008045484 A1 | 4/2008 |
| WO | 2009141238 A1 | 11/2009 |
| WO | 2012/123449 | * 9/2012 |
| WO | 2012123449 A1 | 9/2012 |
| WO | 2015120768 A1 | 8/2015 |

OTHER PUBLICATIONS

Lizarzaburu, Mike, et al., Discovery and optimization of a novel series of GPR142 agonists for the treatment of type 2 diabetes mellitus, Bioorganic & Medicinal Chemistry Letters, Jul. 23, 2012, 5942-5947, 22 ISSN-0960-894X.
Narihiro Toda et al. "Potent and Orally Bioavailable GPR142 Agonists as Novel Insulin Secretagogues for the Treatment of Type 2 Diabetes", ACS Medicinal Chemistry Letters, No. No. 4, Jun. 17, 2013 (Jun. 17, 2013), 790-794.
Wilson, Jonathan, et al., Discovery and development of benzo-[1,2,4]-triazolo-]1,4]-oxazepine GPR142 agonists for the treatment of diabetes, Bioorganic & Medicinal Chemistry Letters, Feb. 26, 2016, 2947-2951, 26.
Toda, Narihiro et al., Potent and Orally Bioavailable GPR142 Agonists as Novel Insulin Secretagogues for the Treatment of Type 2 Diabetes, ACS Medicinal Chemistry, pp. 790-794, ISSN:1948-5875.

\* cited by examiner

*Primary Examiner* — Karl J Puttlitz
(74) *Attorney, Agent, or Firm* — Macharri Vorndran-Jones

(57) ABSTRACT

The present invention provides compounds of the Formula below

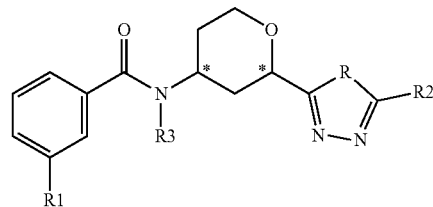

wherein R, R1-R3 are as described herein; methods of treating patients for diabetes using the compounds, and processes for preparing the compounds.

22 Claims, No Drawings

TETRAHYDROPYRANYL BENZAMIDE DERIVATIVES

This invention relates to imidazo benzamide compounds, or pharmaceutically acceptable salts thereof, and therapeutic use thereof. Compounds of this invention are agonists of GPR142.

GPR142 is reported to be expressed in pancreatic cells and associated with the stimulation of insulin secretion under conditions of high blood glucose. Compounds that effectuate GPR142 agonism are desired.

Compounds reported to be GPR142 agonists are disclosed in M. Lizarzaburu, et al. "Discovery and Optimization of a novel series of GPR142 agonists for the treatment of type 2 diabetes," Bioorganic and Medicinal Chemistry Letters 22 (2012) 5942-5947. The compounds reported by Lizarzaburu are a series of phenylalanine related structures.

The present invention provides compounds of Formula 1:

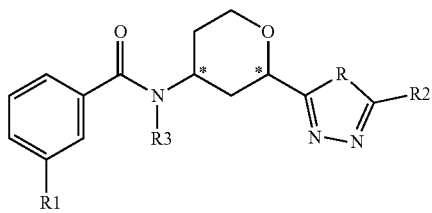

where R is NH or O; R1 is selected from —$CF_3$, —$OCF_3$, and halogen; R2 is selected from:

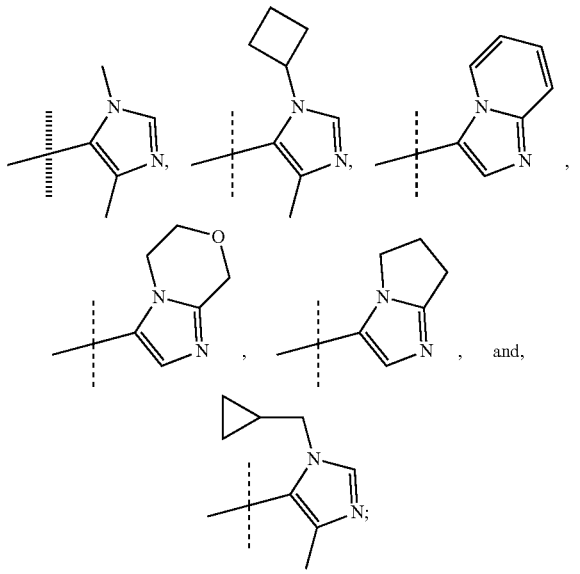

and R3 is $C_{1-3}$alkyl or

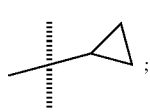

or a pharmaceutically acceptable salt thereof. The ┼ symbol designates where the R2 or R3 group is attached to the remaining portion of the structure. The * symbol in Formula 1 designates a chiral center. Each individual carbon of the chiral centers at positions 2 and 4 on the tetrahydropyranyl ring can exhibit either the R or S configuration. Preferred compounds of the present invention have the benzamide attached to the carbon at the 4 position and the triazolyl or oxodiazolyl ring attached to the carbon at the 2 position of the tetrahydropyranyl ring in a cis configuration relative to each other.

In one embodiment, the present invention provides a compound of Formula 2

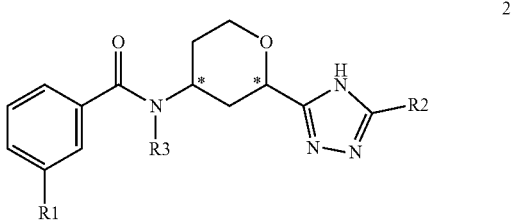

where R1 is selected from —$CF_3$, —$OCF_3$, and halogen; R2 is selected from:

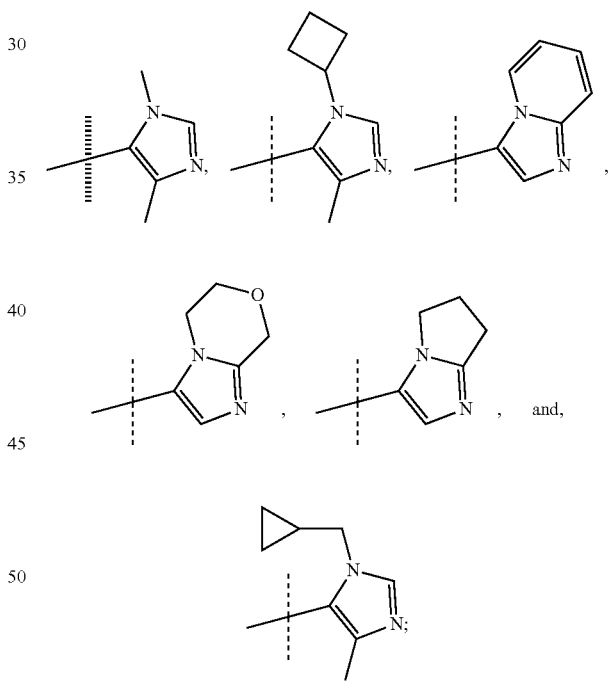

and R3 is $C_{1-3}$alkyl or

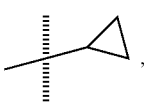

or a pharmaceutically acceptable salt thereof.

In another embodiment, the present invention provides a compound of the Formula 3:

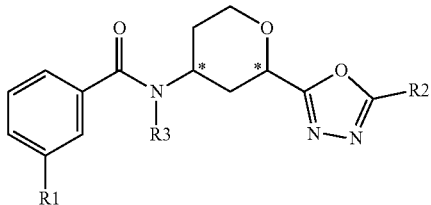

where R1 is selected from —CF$_3$, —OCF$_3$, and halogen; R2 is selected from:

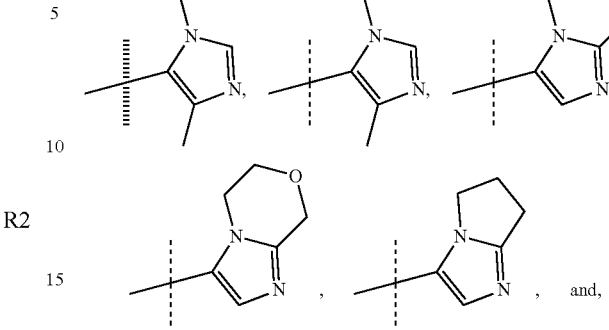

and R3 is C$_{1-3}$alkyl or

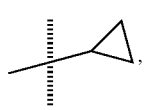

or a pharmaceutically acceptable salt thereof.

In one form, the present invention provides compounds according to any one of Formulae 1-3 where the groups attached to the two chiral centers on the tetrahydropyranyl ring are in a cis configuration relative to each other.

In one form, the present invention provides compounds according to any one of Formulae 1-3 where R1 is selected from: —CF$_3$, —OCF$_3$, F, Cl, and Br. More preferable R1 is selected from: —CF$_3$, —OCF$_3$, and Cl. Still more preferably R1 is —CF$_3$ or —OCF$_3$. Still yet more preferably R1 is CF$_3$.

In another form, the present invention provides compounds according to any one of Formulae 1-3 where R1 is —OCF$_3$ or Cl.

In another form, the present invention provides compounds according to any one of Formulae 1-3 wherein R1 is: —CF$_3$, —OCF$_3$, halogen; and R2 is selected from

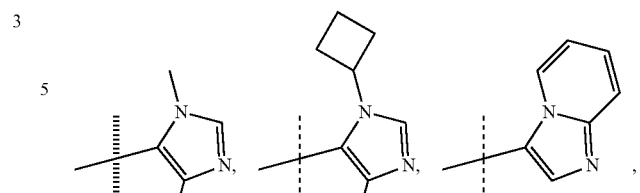

or a pharmaceutically acceptable salt thereof. In preferred compounds according to Formulea 1-3 R1 is selected from: —CF$_3$, —OCF$_3$, and Cl; and R2 is selected from

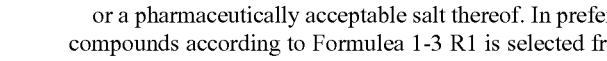
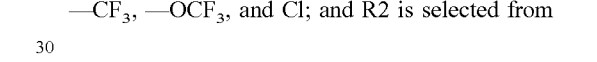
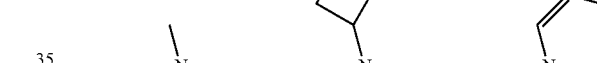

In more preferred compounds according to Formula 1-3, R2 is selected from

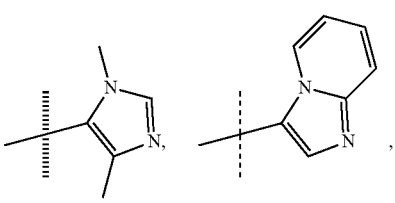

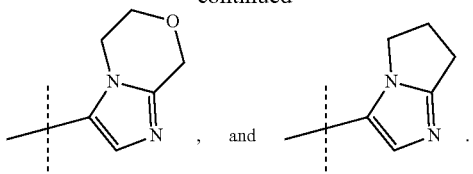

In more preferred compounds according to Formula 1-3, R2 is selected from

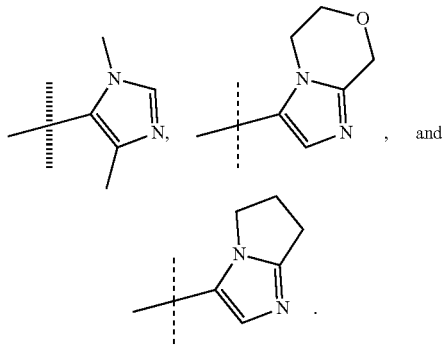

In yet more preferred compounds according to Formula 1-3, R2 is

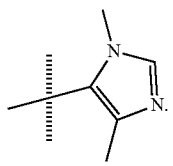

In another form, the present invention provides compounds according to any one of Formulae 1-3 wherein R3 is —CH₃.

In an embodiment of the invention, the present invention provides a compound, selected from:
Cis-(chiral)-N-[(2-[5-(1,4-Dimethyl-1H-imidazol-5-yl)-4H-1,2,4-triazol-3-yl]tetrahydro-2H-pyran-4-yl]-N-methyl-3-(trifluoromethyl)benzamide isomer 1
Cis-(chiral)-3-Chloro-N-[2-[5-(1,4-Dimethyl-1H-imidazol-5-yl)-4H-1,2,4-triazol-3-yl]tetrahydro-2H-pyran-4-yl]-N-methyl-benzamide isomer 1, and
Cis-(chiral)-N-[2-[5-(1,4-Dimethyl-1H-imidazol-5-yl)-4H-1,2,4-triazol-3-yl]tetrahydro-2H-pyran-4-yl]-N-methyl-3-(trifluoromethoxy)benzamide isomer 1;
or a pharmaceutically acceptable salt thereof.

In another embodiment, the present invention provides a compound which is:

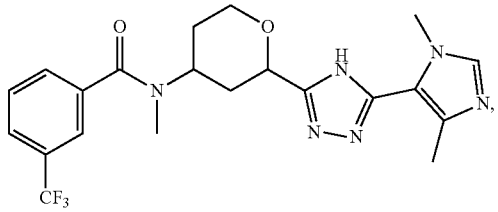 [SMILES: Cc1ncn(C)c1-c1nnc(C2CC(N(C)C(=O)c3cccc(C(F)(F)F)c3)CCO2)[nH]1]

or a pharmaceutically acceptable salt thereof.

The present invention also provides compounds of the Formula 4

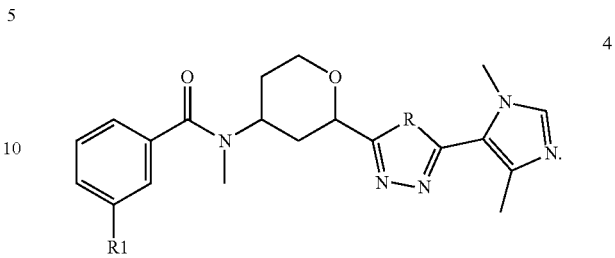

wherein R is selected from the group consisting of O and NH; R1 is selected from the group consisting of —CF₃, —OCF₃, and Cl; or a pharmaceutically acceptable salt thereof.

In an embodiment of the invention the compound of Formula 4 is:

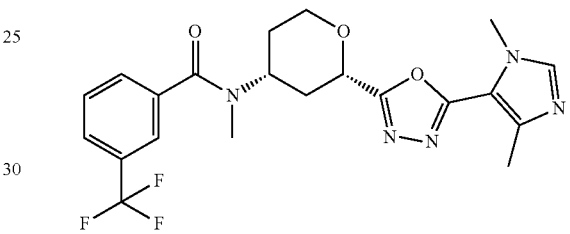

or a pharmaceutically acceptable salt thereof.

In an embodiment of the invention the compound according to Formula 4 is:

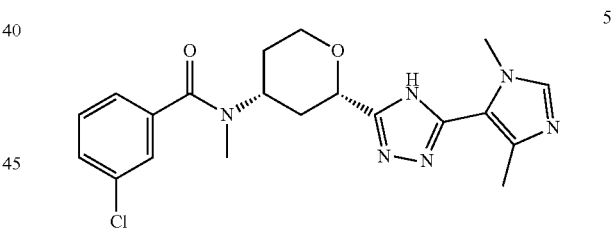

or a pharmaceutically acceptable salt thereof.

In an embodiment, the invention the compound according to Formula 4 is:

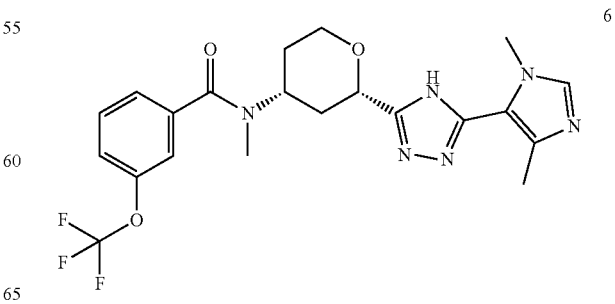

or a pharmaceutically acceptable salt thereof.

In an embodiment, the present invention provides a compound according to Formula 4 wherein R1 is NH; R is selected from: —$CF_3$, Cl, and —$OCF_3$; or a pharmaceutically acceptable salt thereof. In another embodiment, R1 is NH; R is Cl or —$OCF_3$; or a pharmaceutically acceptable salt thereof.

In an embodiment, the present invention provides a compound according to Formula 4 wherein, R1 is O; R is selected from —$CF_3$, Cl, and —$OCF_3$; or a pharmaceutically acceptable salt thereof. In an embodiment, R1 is O; R is —$CF_3$ or —$OCF_3$; or a pharmaceutically acceptable salt thereof.

In an embodiment, for a compound according to Formulae 1-4, the orientation of the functional groups at the 2 and 4 position of the tetrahydropyran are in the cis configuration relative to each other.

The invention provides a pharmaceutical composition, comprising a compound of Formulae 1-4, or a pharmaceutically acceptable salt thereof, and at least one additional pharmaceutically acceptable component selected from the group of: a carrier, a diluent, and an excipient.

The present invention can also include a compound according to Formulae 1-4 and an second pharmaceutically active agent. The skilled artisan will recognize that the second pharmaceutically active agent is suitable for administration sequentially, simultaneously, or concomitantly in combination with a GPR142 agonist. In an embodiment, the second pharmaceutical agent is an agent effective for treating diabetes. In another embodiment, the second pharmaceutical agent is, for example, metformin.

The invention provides a method for treating diabetes in a mammal in need thereof, comprising administering to the mammal an effective amount of a compound of Formulae 1-4 or a pharmaceutically acceptable salt thereof.

The invention also provides a method for treating type II diabetes in a mammal in need thereof, comprising administering to the mammal an effective amount of a compound of Formulae 1-4 or a pharmaceutically acceptable salt thereof. In another embodiment the present invention provides a compound of Formula 1-4, or a pharmaceutically acceptable salt thereof for use in therapy. In another embodiment the present invention provides a compound of Formulae 1-4, or a pharmaceutically acceptable salt thereof for use in therapy, where the therapy is the treatment of type II diabetes. Further, provided is a compound of Formulae 1-4 or a pharmaceutically acceptable salt thereof, for use in the manufacture of a medicament.

Compounds of the present invention are GPR142 agonists, and the invention contemplates methods for treating a disease or condition associated with a decrease in GPR142. Compounds of the present invention may be useful in the treatment of a disease or condition associated with the modulation of GPR142.

As used herein, the term "effective amount" refers to the amount or dose of a compound of the invention or a pharmaceutically acceptable salt thereof, which upon single or multiple dose administration to the mammal, provides the desired effect in the mammal. It will be understood that the amount of active agent actually administered will be determined by a physician or veterinarian, in light of the relevant circumstances, including the condition to be treated, the chosen route of administration, the actual active agent administered, the age, weight, and response of the individual mammal, and the severity of the symptoms and other relevant circumstances. In one example the effective amount may be the amount of a compound of the invention effective to lower blood or plasma glucose levels.

The compounds of the present invention can be provided as a pharmaceutically acceptable salt. "Pharmaceutically-acceptable salt" refers to salts of a compound of the invention considered to be acceptable for clinical and/or veterinary use. Examples of pharmaceutically acceptable salts and methodologies for preparing them can be found in P. Stahl, et al., Handbook of Pharmaceutical Salts: Properties, Selection and Use, (VCHA/Wiley-VCH, 2002) and S. M. Berge, et al., "Pharmaceutical Salts," *Journal of Pharmaceutical Sciences*, Vol. 66, No. 1, January 1977.

The term "pharmaceutically acceptable carrier, diluent, or excipients" means that the carrier, diluent, and excipients are pharmaceutically compatible with the other ingredients of the composition. Pharmaceutical compositions and processes for their preparation are known and examples can be found in "Remington: The Science and Practice of Pharmacy", A. Gennaro, et al. Eds. 21$^{st}$ Ed., Mack Publishing Co., 2005. Non-limiting examples of pharmaceutically acceptable carriers, diluents, and excipients include the following: saline, water, starch, sugars, mannitol, and silica derivatives; binding agents such as carboxymethyl cellulose and other cellulose derivatives, alginates, gelatin, and poly-vinyl-pyrrolidone; kaolin, bentonite; and polyethyl glycols.

Individual isomers, enantiomers, and diastereomers may be separated or resolved by one of ordinary skill in the art at any convenient point in the synthesis of compounds of the invention. (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples. The skilled artisan will recognize that the first eluting isomer may vary depending on the elution conditions. Additionally, the intermediates described in the following Schemes, Preparations, and Examples contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, Protective Groups in Organic Synthesis, (T. Greene and P. Wuts, eds., 2d ed. 1991).

The abbreviations used herein are defined according to *Aldrichimica Acta*, Vol. 17, No. 1, 1984. Other abbreviations are defined as follows: "AUC" refers to area under the curve; "BSA" refers to Bovine Serum Albumin; "Burgess reagent" refers to methyl N-(triethylammoniumsulfonyl) carbamate; "CDI" refers 1,1'-carbonyldiimidazole; "DCC" refers to 1,3-dicyclohexylcarbodiimide; "DIC" refers to 1,3-diisopropylcarbodiimide; "DCM" refers to dichloromethane or methylene chloride; "DMEM" refers to Dulbecco's Modified Eagle's Medium; "DMF" refers to dimethylformamide; "DMSO" refers to dimethylsulfoxide; "$EC_{50}$" refers to the effective concentration at half the maximal response; "ee" refers to enantiomeric excess; "$ED_{50}$", refers to the effective dose in milligrams per kilogram ("mpk") for 50% of subjects receiving the test compound; "$ED_{80}$" refers to the effective dose in milligrams per kilogram ("mpk") for 80% of subjects receiving the test compound; "EDCI" refers to 1-(3-dimethylaminopropyl)-3-ethylcarbodiimide hydrochloride; "EtOAc" refers to ethyl acetate; "EtOH" refers to ethanol; "FA" refers to formic acid; "FBS" refers to Fetal Bovine Serum; "GDIS" refers to glucose-dependent Insulin Secretion; "HATU" refers to (1-[bis(dimethylamino)methylene]-1H-1,2,3-triazolo[4,5-b]pyridinium 3-oxid hexafluorophosphate); "HBSS" refers to Hank's Balanced Salt Solution; "HBTU" refers to (1H-benzotriazol-1-yloxy) (dimethylamino)-N,N-dimethylmethaniminium hexafluorophosphate; "HEK" refers to human embryonic kidney; "HEPES" refers to 4-(2-hydroxyethyl)-1-piperazineethanesulfonic acid; "hr or hrs" refers to hour or hours; cated, are as previously defined. The reagents and starting materials are generally readily available to one of ordinary skill in the art. Others may be made by standard techniques of organic and heterocyclic chemistry and the procedures described in the Preparations and Examples which follow, including any novel procedures.

The following preparations and examples further illustrate the invention and represent typical synthesis of the compound of Formulae 1-4.

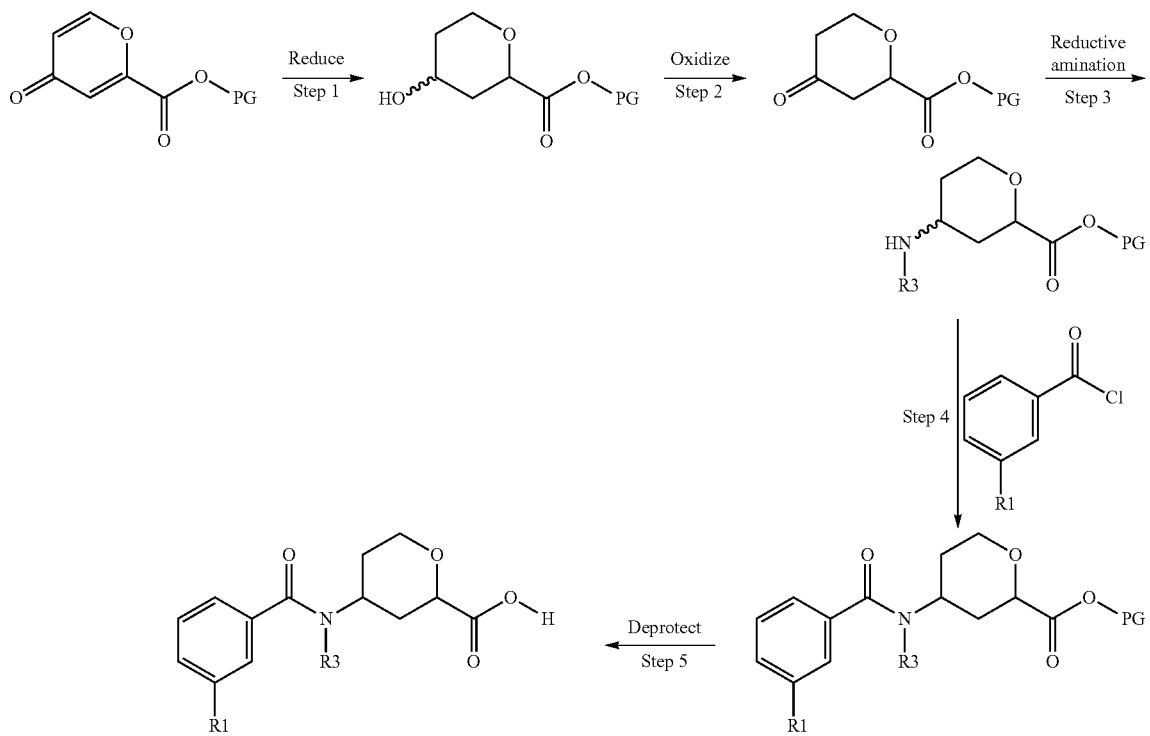

Scheme 1

"HTRF®" refers to homogeneous time resolved fluorescence; "IP-1" refers to Inositol phosphate-1; "IPGTT" refers to intraperitoneal glucose tolerance tests; "KRB" refers to Krebs Ringer Buffer; "MeOH" refers to methyl alcohol or methanol; "min" refers to minutes; "MTBE" refers to methyl t-butyl ether; "NBS" refers to N-bromosuccinimide; "PCC" refers to pyridinium chlorochromate; "PE" refers to petroleum ether; "PyBOP" refers to (benzotriazol-1-yloxytripyrrolidinophosphonium hexafluorophosphate); "PyBrOP" refers to bromo(tri-pyrrolidinyl)phosphoniumhexafluorophosphate; "rpm" refers to revolutions per minute; "RPMI" refers to Roswell Park Memorial Institute; "$R_t$" refers to retention time; and "THF" refers to tetrahydrofuran.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formulae 1-4, or salts thereof. The products of each step in the schemes below can be recovered by conventional methods well known in the art, including extraction, evaporation, precipitation, chromatography, filtration, trituration, and crystallization. In the Preparations and Schemes below, all substituents unless otherwise indi- Scheme 1 depicts the formation of a substituted benzoyl amino tetrahydropyran carboxylic acid. The product of Step 1 is prepared by the reduction of the pyranone under hydrogenation conditions. For example, the pyranone can be reduced with a palladium catalyst such as 10% palladium on carbon under an atmosphere of hydrogen to give the 4-hydroxy-2-protected carboxylate tetrahydropyran. The hydroxyl group of the product of Step 1 can be oxidized to the ketone compound of Step 2. A reductive amination provides the product of Step 3. A nucleophilic addition using an appropriate 3-acyl chloride, provides the benzoyl amino tetrahydropyran in Step 4. The ester of the product of Step 4 can be deprotected to give the deprotected substituted benzoyl amino tetrahydropyran carboxylic acid product of Step 5.

Scheme 2

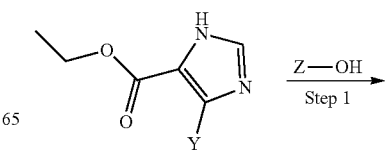

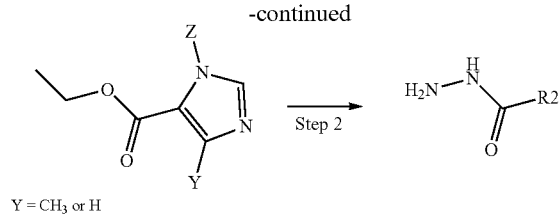

Y = CH₃ or H

In Scheme 2, a substituted imidazole-5-carboxylate can be alkylated under nitrogen in a modified Mitsunobu reaction to give the N-alkylated imidazole product of Step 1. The ester of the N-alkylated imidazole can be converted to the hydrazide with aqueous hydrazine. When R2 is a bicyclic group, the synthetic procedures are more fully described in the Preparations and Examples below.

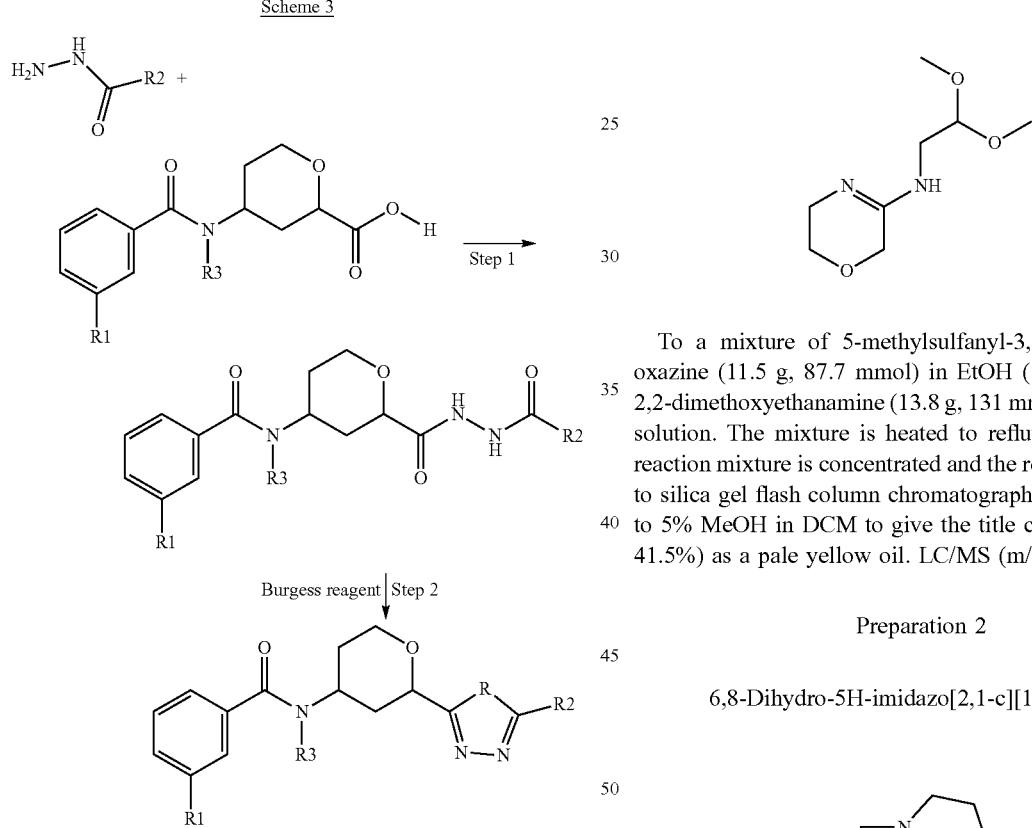

In Scheme 3, the hydrazide imidazole product of Scheme 2, Step 2, is coupled with the substituted benzoyl amino tetrahydropyran carboxylic acid product of Scheme 1, Step 5, to form the 1,3,4-oxadiazole ring for compounds of Formulae 1 and 2 for R is O. The carboxylic acid product of Scheme 1, Step 5 is added to the hydrazide product of Scheme 2, Step 2 with an organic base. The intermediate carbonyl hydrazine product of Scheme 3, Step 1 can be isolated and purified or the crude material can be carried through Step 2 without isolation. In Step 2, the Burgess reagent is added to complete the oxadiazole formation to give compounds of Formulae 1 and 2 for R═O. Other coupling reagents, such as HBTU, PyBOP, PyBrOP or more traditional coupling reagents such as DCC, DIC, EDCI, or CDI can be used to give the intermediate product of Step 2. The oxadiazole can be converted to the triazole using ammonium acetate with an acid to give compounds of Formulae 1 and 3 for R═N.

In an optional step, a pharmaceutically acceptable salt of a compound of Formulae 1-4 can be formed by reaction of an appropriate free base with an appropriate pharmaceutically acceptable acid in a suitable solvent under standard conditions.

Preparations

Preparation 1

N-(2,2-Dimethoxyethyl)-3,6-dihydro-2H-1,4-oxazin-5-amine

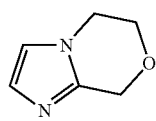

To a mixture of 5-methylsulfanyl-3,6-dihydro-2H-1,4-oxazine (11.5 g, 87.7 mmol) in EtOH (120 mL) is added 2,2-dimethoxyethanamine (13.8 g, 131 mmol) to give a clear solution. The mixture is heated to reflux for 48 hrs. The reaction mixture is concentrated and the residue is subjected to silica gel flash column chromatography eluting with 0% to 5% MeOH in DCM to give the title compound (13.7 g, 41.5%) as a pale yellow oil. LC/MS (m/z): 189 (M+H).

Preparation 2

6,8-Dihydro-5H-imidazo[2,1-c][1,4]oxazine

To a mixture of N-(2,2-dimethoxyethyl)-3,6-dihydro-2H-1,4-oxazin-5-amine (13.7 g, 36.4 mmol) in MeOH (130 mL) is added hydrochloric acid (12.18 mol/L) in water (100 mL, 1218 mmol) to give a colorless solution. The mixture is heated to reflux for 3 hrs. The reaction mixture is concentrated and the pH is adjusted to 9 with NaHCO₃. The residue is subjected to silica gel flash column chromatography eluting with 30% to 50% EtOAc in PE to give the title compound (4.20 g, 88.3%) as a pale yellow oil. LC/MS (m/z): 125 (M+H).

Preparation 3

3-Bromo-6,8-dihydro-5H-imidazo[2,1-c][1,4]oxazine

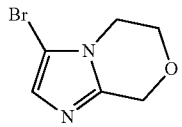

To a mixture of 6,8-dihydro-5H-imidazo[2,1-c][1,4]oxazine (3.90 g, 31.4 mmol) in acetonitrile (40 mL) is added NBS (5.59 g, 31.42 mmol) at 0° C. The mixture is stirred at 0° C. for 30 minutes. The reaction mixture is evaporated in vacuo, dissolved in water (200 mL), and extracted with EtOAc (5×50 mL). The combined organic extracts are washed with brine (30 mL), dried over $Na_2SO_4$. The volatiles are evaporated in vacuo to give the title compound (4.60 g, 68.5%) as a yellow solid. LC/MS (m/z): 203/205 (M+H).

Preparation 4

Ethyl 6,8-dihydro-5H-imidazo[2,1-c][1,4]oxazine-3-carboxylate

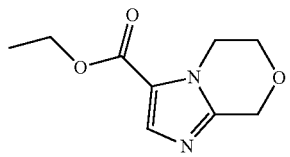

To a mixture of 3-bromo-6,8-dihydro-5H-imidazo[2,1-c][1,4]oxazine (3.86 g, 19.0 mmol) and trimethylamine (7.95 mL, 57.0 mmol) in EtOH (40 mL) is added 1,1-bis(diphenylphosphino)ferrocene (400 mg, 0.722 mmol) at room temperature. The mixture is heated to 80° C. at 345 kPa under a carbon monoxide atmosphere for 24 hrs. The reaction mixture is filtered and the filtrate is evaporated in vacuo. The residue is subjected to silica gel flash column chromatography eluting with 10% to 25% EtOAc in PE to give the title compound (3.20 g, 73.8%) as a yellow solid. LC/MS (m/z): 197 (M+H).

Preparation 5

Methyl 4-hydroxytetrahydro-2H-pyran-2-carboxylate

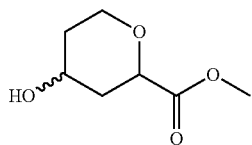

To a solution of methyl 4-oxopyran-2-carboxylate (200 g, 1.3 mol) in EtOAc (1 L) at room temperature, 10% Pd/C (20 g, 50% wt $H_2O$) is added. The mixture is degased under reduced pressure and flushed with $H_2$, stirred at 50° C. under a $H_2$ atmosphere (0.3 MPa) for 24 hrs. The mixture is filtered and the volatiles are removed to give the title compound (200 g, 96%) as a yellow oil. LC/MS (m/z): 161 (M+H).

Preparation 6

Methyl 4-oxotetrahydro-2H-pyran-2-carboxylate

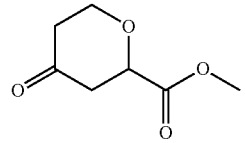

To a solution of methyl 4-hydroxytetrahydro-2H-pyran-2-carboxylate (500 g, 3.1 mol) in DCM (5 L) at room temperature diatomaceous earth (500 g) is added. PCC (500 g, 2.3 mol) is added in small portions over 20 minutes at room temperature. The mixture is stirred at room temperature for 18 hrs. The mixture is filtered through a pad of silica gel and washed with DCM. The mixture is concentrated to provide a residue. The residue is subjected to silica gel column chromatography (PE/EtOAc, 3/2) to give the title compound (430 g, 76%) as pale yellow oil. GC-MS (m/z) (ESI): 158 (M+).

Preparation 7

Methyl 4-(methylamino)tetrahydro-2H-pyran-2-carboxylate

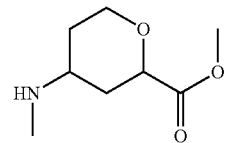

Methyl 4-oxotetrahydro-2H-pyran-2-carboxylate (16.9 g, 106.9 mmol), methylammonium chloride (18.0 g, 267.1 mmol) and MeOH (300 mL) are combined. The mixture is cooled to 0° C., then sodium carbonate (34.0 g, 320.6 mmol) and sodium triacetoxyborohydride (45.3 g, 213.7 mmol) are added. The mixture is stirred at room temperature overnight. The mixture is filtered and washed with MeOH (50 mL). The mixture is concentrated to give a residue. The residue is filtered through a short pad of silica gel eluting with 1/20 MeOH in DCM to remove the inorganic salt. The filtrate is concentrated to give the title compound (18.5 g, 99%) as yellow oil. LC/MS (m/z): 174 (M+H).

Alternate Preparation 7

Methyl 4-oxotetrahydro-2H-pyran-2-carboxylate (1 kg, 6.3 mol) is dissolved in MeOH (15 L) and the mixture is cooled to 0° C. Methylamine HCl (854.5 g, 12.6 mol) is added and the mixture is stirred for 30 minutes at 0° C. Sodium carbonate (2 kg, 18.9 mol) is added and the mixture is stirred for 30 minutes at 0° C. Sodium triacetoxyborohydride (2.7 g, 12.7 mol) is added at 0° C. The mixture is stirred for 17 hrs. at 5-25° C. The mixture is then filtered and washed with MeOH (5 L) and concentrated under vacuum. The residue is diluted with 1 M $Na_2CO_3$ (10 L) and DCM (15 L) and the layers separated. The aqueous layer is extracted with DCM (10 L). The organic extracts are combined and concentrated to give the title product (1.01 kg, 96%), which can be used without further purification.

Preparation 8

Cis-(chiral)-Methyl-4-[N-methyl-3-(trifluoromethoxy)benzamido]tetrahydro-2H-pyran-2-carboxylate, Isomer 1

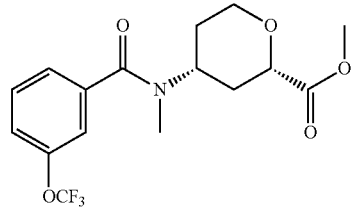 [SMILES: COC(=O)[C@@H]1C[C@H](N(C)C(=O)c2cccc(OC(F)(F)F)c2)CCO1]

To a solution of methyl 4-(methylamino)tetrahydro-2H-pyran-2-carboxylate (18.5 g, 106.8 mmol) and triethylamine (44.7 mL, 320.4 mmol) in DCM (200 mL) and THF (150 mL) at 0° C., 3-(trifluoromethoxy)benzoyl chloride (21.0 g, 94.0 mmol) is added. The mixture is stirred at room temperature for 2 hrs. Saturated $NaHCO_3$ (150 mL) is added. The mixture is extracted with EtOAc (3×200 mL), dried over $Na_2SO_4$, filtered, and concentrated. The residue is subjected to silica gel flash chromatography eluting with 0-40% EtOAc in PE to give the racemic title compound, which is resolved with chiral chromatography to give the title compound: Isomer 1, (4.8 g, 13%), $R_t$=2.96 min, LC/MS (m/z): 362 (M+H). 98% ee. Instrument: SFC-80 (Thar, Waters), column: OZ—H 20×250 mm, 5 μm, column temperature: 35° C., mobile phase: $CO_2$/MeOH (0.1% diethylamine)=90/10, flow rate: 80 mL/min, back pressure: 100 bar, detection wavelength: 214 nm, cycle time: 2.0 min, sample solution: 12000 mg dissolved in 380 mL MeOH, injection volume: 1 mL.

Preparation 9

Cis-(chiral)-Methyl-4-[N-methyl-3-(trifluoromethyl)benzamido]tetrahydro-2H-pyran-2-carboxylate, Isomer 1

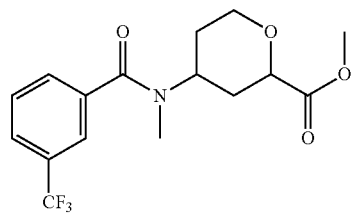 [SMILES: COC(=O)C1CC(N(C)C(=O)c2cccc(C(F)(F)F)c2)CCO1]

Preparation 9a

Cis-(chiral)-Methyl-4-[N-methyl-3-(trifluoromethyl)benzamido]tetrahydro-2H-pyran-2-carboxylate, Isomer 2

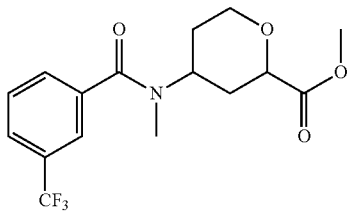 [SMILES: COC(=O)C1CC(N(C)C(=O)c2cccc(C(F)(F)F)c2)CCO1]

The title compounds are prepared essentially as described in Preparation 8 using 3-(trifluoromethyl) benzoyl chloride. The two isomers can be separated using chiral chromatography. Isomer 1: (17.8 g, 41%), $R_t$=2.64 minutes, LC/MS (m/z): 346 (M+H), 99% ee and Isomer 2: (17.0 g, 39%), $R_t$=3.86 minutes, LC/MS (m/z): 346 (M+H), 90% ee. Instrument: SFC-80 (Thar, Waters), column: AD 50×250 mm, 5 μm, column temperature: 35° C., mobile phase: $CO_2$/MeOH (0.1% diethylamine)=85/15, flow rate: 160 mL/min, back pressure: 100 bar, detection wavelength: 214 nm, cycle time: 5.0 min, sample solution: 10.5 g dissolved in 200 mL MeOH, injection volume: 4 mL.

Alternate Preparation 9

Methyl 4-[methyl-[3-trifluoromethyl)benzoyl]amino]tetrahydropyran-2-carboxylate

Methyl 4-(methylamino)tetrahydro-2H-pyran-2-carboxylate (1.05 kg, 6.06 mol), DCM (20 L) and triethylamine (1.5 kg, 14.5 mol) are added together and the mixture is cooled to 0° C. 3-(Trifluoromethyl) benzoyl chloride is added dropwise at 0-5° C. and the mixture is stirred for 17 hrs at 0-20° C. Water (10 L) is added. The mixture is stirred for 30 min and the layers are separated. The organic layer is retained and the volatiles are removed to provide a solid. The solid is dissolved in DCM (1 L). MTBE (5 L) is added followed by the dropwise addition of n-heptane (15 L) at 10-20° C. The mixture is cooled to 0-5° C. and stirred for 16 hrs. A solid is collected and dried under vacuum below 20° C. to give the title compound (651.0 g). The crude product is subjected to silica gel chromatography followed by SFC separation to give the title compound (538 g, 26%). Chiral purification conditions: Instrument TharSFC 350; Mobile phase A ($CO_2$) B (EtOH); flow rate A 150 g minutes and B 30 mL/minutes; column AD (250*50 mm, 10 μm); wavelength 220 nm; back pressure 100 Bar; injection amount 400 mg/injection every 3 minutes. A second purification is completed to improve purity using a mobile phase of A ($CO_2$) B (isopropanol 60 mL/minutes to give the title compound with an ee of 99.4%, $R_t$ 7.29 min.

Preparation 10

Cis-(chiral)-Methyl-4-(3-chloro-N-methylbenzamido)tetrahydro-2H-pyran-2-carboxylate, Isomer 1

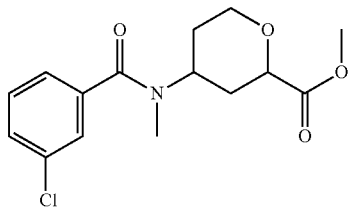 [SMILES: COC(=O)C1CC(N(C)C(=O)c2cccc(Cl)c2)CCO1]

Preparation 10a

Cis-(chiral)-Methyl-4-(3-chloro-N-methylbenzamido)tetrahydro-2H-pyran-2-carboxylate, Isomer 2

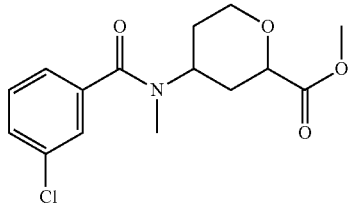 [SMILES: COC(=O)C1CC(N(C)C(=O)c2cccc(Cl)c2)CCO1]

The title compound is prepared essentially as described in Preparation 8 using 3-chloro-benzoyl chloride. The two isomers are separated using chiral chromatography. Isomer 1: (5.07 g, 51%), $R_t$=2.16 minutes, LC/MS (m/z): 312 (M+H), 100% ee and Isomer 2. (4.74 g, 47%), $R_t$=3.14 minutes, LC/MS (m/z): 312 (M+H), 98% ee. Instrument: SFC-5 (Thar, Waters), column: AY 50×250 mm, 10 μm, mobile phase: $CO_2$/isopropanol (0.05% diethylamine)=65/35, flow rate: 180 mL/min, detection wavelength: 260 nm, injection volume: 2 mL.

Preparation 11

Ethyl 1,4-dimethyl-1H-imidazole-5-carboxylate

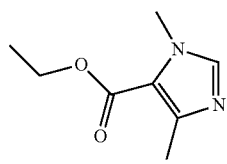

To a mixture of ethyl 4-methyl-1H-imidazole-5-carboxylate (7.30 g, 45.9 mmol) in THF (60 mL) is added MeOH (2.23 mL, 55.1 mmol) and triphenylphosphine (14.8 g, 55.1 mmol). The reaction is cooled to 0° C. under $N_2$ and diethyl azodicarboxylate (9.0 mL, 17.6 mmol) is added dropwise. The mixture is warmed to room temperature and stirred overnight. The volatiles are evaporated in vacuo. Ether (50 mL) is added. The mixture is stirred at room temperature for 30 minutes, filtered, the filter cake is washed with ether (50 mL). The filtrate and ether washings are combined and are sequentially washed with water (30 mL) and brine (30 mL). The organic phase is dried over $Na_2SO_4$, evaporated in vacuo to provide the crude product. The crude product is subjected to silica gel flash column eluting with 30% EtOAc in hexanes to EtOAc to give the title compound (5.13 g, 59.8%) as a yellow oil. LC/MS (m/z): 169 (M+H).

Preparation 12

Ethyl 3-(cyclopropylmethyl)-5-methyl-imidazole-4-carboxylate

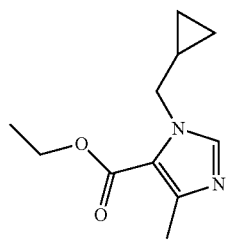

Prepare the title compounds essentially as described in Preparation 11 replacing MeOH with the appropriate alcohol. ES/MS (m/z) 209.

Preparation 13

Ethyl 3-cyclobutyl-5-methyl-imidazole-4-carboxylate

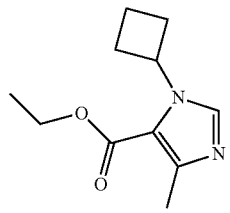

Prepare the title compounds essentially as described in Preparation 11 with the modification that N,N-diisopropylethylamine (1.2 equivalent) is added to the reaction before diethyl azodicarboxylate is added. ES/MS (m/z) 209.

Alternate Preparation 11

Ethyl 1,4-dimethyl-1H-imidazole-5-carboxylate

Ethyl 4-methyl-1H-imidazole-5-carboxylate (690 g, 4.5 mol) triphenylphosphine (1.76 kg, 6.6 mol) and THF (5.5 L) are added together and the mixture is degassed with nitrogen for 30 min MeOH (1.4 kg) is added and the mixture is cooled to 0-5° C. Diethyl azodicarboxylate (1.17 kg, 6.7 mol) is added dropwise at 0-5° C. The mixture is warmed to 15-20° C. and stirred for 3 hrs. The mixture is concentrated to 4-5 volumes under vacuum and poured into a solution of MTBE (5 volumes) and n-heptane (5 volumes). This mixture is stirred for 30 mins and then is filtered. The filter cake is slurried with MTBE (5 volumes) and n-heptane (5 volumes). The mixture is filtered again and the filtrate is collected. The volatiles are removed to give the title compound (1.52 kg, 100% crude) which can be used without further purification.

Preparation 14

Methyl 6,7-dihydro-5H-pyrrolo[1,2-yl]imidazole-3-carboxylate

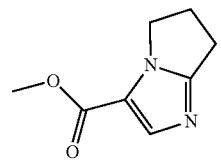

3-Bromo-6,7-dihydro-5H-pyrrolo[1,2-a]imidazole (2.26 g, 11.5 mmol) and THF (40 mL) are added together. n-Butyllithium (1.6 mol/L) in hexanes (8.6 mL, 13.8 mmol) is added at −78° C. and the mixture is stirred at −78° C. for 30 min. Dimethyl carbonate (1.16 mL, 13.8 mmol) is added. The mixture is warmed to room temperature and is stirred for another 3.5 hrs. The volatiles are evaporated in vacuo. The residue is dissolved in water and the aqueous mixture is extracted with EtOAc (2×100 mL). The organic extracts are combined and are washed with brine (30 mL). The organic layer is dried over Na₂SO₄ and the volatiles are evaporated in vacuo. The crude product is subjected to silica gel flash column chromatography eluting with 2% to 8% MeOH in DCM to give the title compound (1.23 g, 58.0%) as a pink solid. LC/MS (m/z): 167 (M+H).

Preparation 15

1,4-Dimethyl-1H-imidazole-5-carbohydrazide

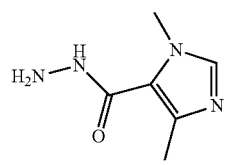

To a solution of ethyl 1,4-dimethyl-1H-imidazole-5-carboxylate (2.6 g, 14 mmol) in EtOH (16 mL) at room temperature is added hydrazine in water (4 mL, 102.9 mmol) slowly over 2 min. The mixture is then stirred at 100° C. overnight. The mixture is concentrated and lyophilized to give the title compound (2.3 g, 97%) as a white solid, which can be used without further purification. LC/MS (m/z): 155 (M+H).

The following compounds are prepared essentially as described in Preparation 15.

TABLE 1

| Prep | Chemical Name | Structure | ES/MS (m/z) (M + H) |
|---|---|---|---|
| 16 | 3-(Cyclopropylmethyl)-5-methyl-imidazole-4-carbohydrazide | 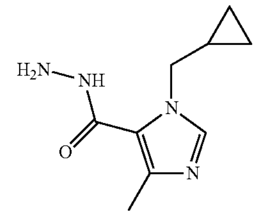 | 195 |
| 17 | 6,7-Dihydro-5H-pyrrolo[1,2-a]imidazole-3-carbohydrazide | 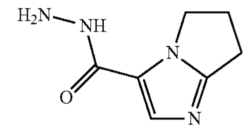 [SMILES: NNC(=O)c1cnc2n1CCC2] | 167 |
| 18 | 6,8-Dihydro-5H-imidazo[2,1-c][1,4]oxazine-3-carbohydrazid | 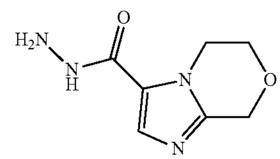 [SMILES: NNC(=O)c1cnc2n1CCOC2] | 183 |
| 19 | 3-Cyclobutyl-5-methyl-imidazole-4-carbohydrazide | 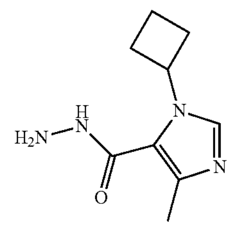 | 195 |

Alternate Preparation 15

1,4-Dimethyl-1H-imidazole-5-carbohydrazide

Ethyl 1,4-dimethyl-1H-imidazole-5-carboxylate (1.74 kg, 10.3 mol), hydrazine (3.2 kg, 84.8 mol) in water (3.2 L) and EtOH (4.2 L) are added together. The mixture is heated to 75-80° C. for 70 hrs. The mixture is cooled to 40° C. The volatiles are removed in vacuo. The residue is slurried with MeOH (10 volumes) for 30 minutes and filtered. The filtrate is concentrated. EtOAc is added and the volatiles are removed in vacuo. The residue is subjected to silica gel column chromatography eluting with 5% MeOH in DCM followed by slurrying the product with EtOAc (20 volumes) to give the title product (131 g, 38%, 99.9% purity).

Preparation 20

Imidazo[1,2-a]pyridine-3-carbohydrazide

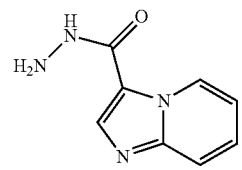 [SMILES: NNC(=O)c1cnc2ccccn12]

Ethyl imidazo[1,2-a]pyridine-3-carboxylate (0.90 g, 4.7 mmol) and hydrazine (1.0 mL, 13 mmol, 40%) are combined in EtOH (10 mL). The mixture is stirred under microwave conditions at 100° C. for 2 hrs. The solvent is removed to give the title compound (0.82 g, 93%) which can be used without further purification. LC/MS (m/z): 177 (M+H).

Preparation 21

Methyl 4-(cyclopropylamino)-tetrahydro-2H-pyran-2-carboxylate

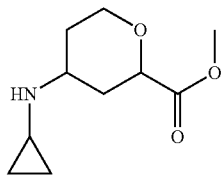

Methyl 4-oxotetrahydro-2H-pyran-2-carboxylate (10.7 g, 67.66 mmol), cyclopropyl amine (9.39 mL, 135.31 mmol) and MeOH (50 mL) are combined. The mixture is cooled to 0° C., and sodium triacetoxyborohydride (28.68 g, 135.31 mmol) is added. The mixture is stirred at room temperature overnight. The mixture is filtered, washed with MeOH (50 mL), and the volatiles are removed in vacuo. The residue is diluted with water (50 mL), then the pH is adjusted to pH=7-8 with saturated $Na_2CO_3$. The mixture is extracted with EtOAc (4×150 mL). The extracts are dried over $Na_2SO_4$, filtered, and the volatiles are removed in vacuo to give the title compound (10.3 g, 76.41%) as a yellow oil. LC/MS (m/z): 200 (M+H).

Preparation 22

Racemic cis-Methyl 4-(N-cyclopropyl-3-(trifluoromethyl)benzamido)-tetrahydro-2H-pyran-2-carboxylate

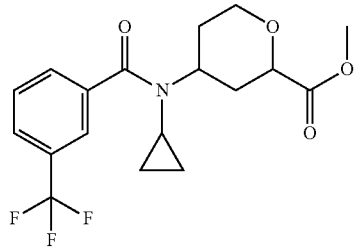 [SMILES: COC(=O)C1CC(N(C(=O)c2cccc(C(F)(F)F)c2)C2CC2)CCO1]

To a solution of methyl 4-(cyclopropylamino)-tetrahydro-2H-pyran-2-carboxylate (10.3 g, 106.8 mmol) and triethylamine (18.0 mL, 129.14 mmol) in DCM (100 mL) at 0° C., is added dropwise 3-(trifluoromethyl)benzoyl chloride (12.0 g, 57.54 mmol). The mixture is warmed to room temperature and stirred overnight. The mixture is concentrated to provide a crude residue. The residue is subjected to silica gel flash column chromatography eluting with 0% to 20% EtOAc in hexanes to give the title compound (11.9 g, 61.99%) as a pale-yellow solid. LC/MS (m/z): 372 (M+H).

Preparation 23

Cis-(chiral)-4-[N-Methyl-3-(trifluoromethyl)benzamido]tetrahydro-2H-pyran-2-carboxylic acid, Isomer 1

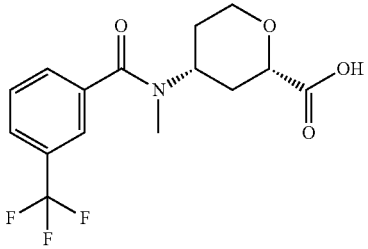 [SMILES: CN(C(=O)c1cccc(C(F)(F)F)c1)[C@@H]1CCO[C@H](C(=O)O)C1]

To a solution of cis-(chiral)-methyl-4-[N-methyl-3-(trifluoromethyl)benzamido]tetrahydro-2H-pyran-2-carboxylate, Isomer 1 (4.32 g, 12.0 mmol) in a mixture of THF (30 mL), MeOH (30 mL) and $H_2O$ (15 mL) is added LiOH (2.52 g, 60 mmol). The mixture is stirred at room temperature for 3 hrs. The mixture is concentrated to provide a residue, and the residue is dissolved in $H_2O$ (30 mL). The aqueous mixture is washed with EtOAc (1×50 mL), and the pH is adjusted to 2 with a 1 M HCl solution. The aqueous mixture is extracted with EtOAc (2×100 mL). The organic extracts are combined and are dried over $Na_2SO_4$. The volatiles are removed in vacuo to give the title compound (4.10 g, 98%) as a white solid. LC/MS (m/z): 332 (M+H).

The following compounds are prepared essentially as described for Preparation 23 using the appropriate benzamido tetrahydro-2H-pyran-2-carboxylate ester.

TABLE 2

| Prep | Chemical Name | Structure | ES/MS (m/z) (M + H) |
|---|---|---|---|
| 24† | Cis-(chiral)-4-(N-Methyl-3-(trifluoromethoxy)benzamido)tetrahydro-2H-pyran-2-carboxylic acid, Isomer 1 | 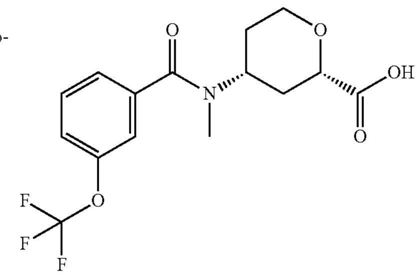 | 348 |
| 25† | Cis-(chiral)-4-(3-Chloro-N-methylbenzamido)tetrahydro-2H-pyran-2-carboxylic acid, Isomer 1 | 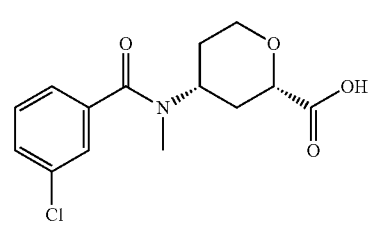 [SMILES: CN(C(=O)c1cccc(Cl)c1)[C@@H]1CCO[C@H](C(=O)O)C1] | 298 |
| 26†† | Racemic Cis-4-(N-Cyclopropyl-3-(trifluoromethyl)benzamido)-tetrahydro-2H-pyran-2-carboxylic acid | 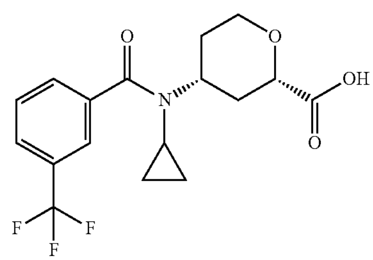 [SMILES: O=C(O)[C@@H]1C[C@H](N(C(=O)c2cccc(C(F)(F)F)c2)C2CC2)CCO1] | 358 |
| 26a | Cis-(chiral)-4-[N-Methyl-3-(trifluoromethyl)benzamido]tetrahydro-2H-pyran-2-carboxylic acid, Isomer 2 | 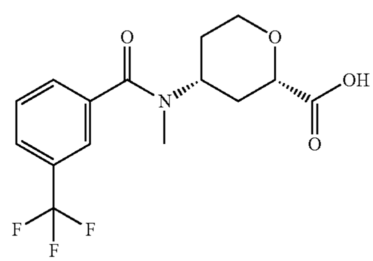 [SMILES: CN(C(=O)c1cccc(C(F)(F)F)c1)[C@@H]1CCO[C@H](C(=O)O)C1] | 332 |

†The mixture is stirred overnight
††The pH is adjusted to 5 with 3M HCl solution

Alternate Preparation 23

Cis-(chiral)-4-[N-Methyl-3-(trifluoromethyl)benzamido]tetrahydro-2H-pyran-2-carboxylic acid, Isomer 1

Cis-(chiral)-Methyl-4-(3-chloro-N-methylbenzamido)tetrahydro-2H-pyran-2-carboxylate, Isomer 1 (438 g, 1.3 mol) is added together with MeOH (1.1 L) and THF (1.1 L). Water (1.1 L) and lithium hydroxide hydrate (181 g, 4.3 mol) are added and the mixture is heated to 25° C. for 3 hrs. The solution is concentrated to 1 L and HCl is added to adjust the pH to 4. The solution is diluted with EtOAc (3 L) and the organic layer is separated. The aqueous layer is extracted with EtOAc (1.5 L), the organic extracts are combined, and the volatiles are removed to give the title compound (415 g, 99%) which can be used without further purification.

Preparation 27

Racemic (Cis)-4-[Cyclopropyl-[3-(trifluoromethyl)benzoyl]amino]tetrahydropyran-2-carboxamide

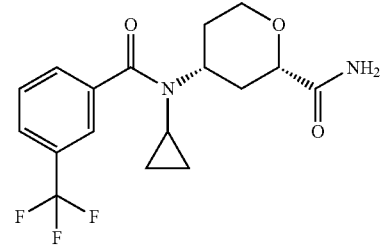 [SMILES: NC(=O)[C@@H]1C[C@H](N(C(=O)c2cccc(C(F)(F)F)c2)C2CC2)CCO1]

To a solution of racemic cis-4-(N-cyclopropyl-3-(trifluoromethyl)benzamido)-tetrahydro-2H-pyran-2-carboxylic acid (2.45 g, 6.51 mmol) in DCM (50 mL) is added HBTU (3.82 g, 9.77 mmol), NH$_4$Cl (0.70 g, 13.0 mmol), and N,N-diisopropylethylamine (2.27 mL, 13.0 mmol). The mixture is stirred at room temperature overnight. The mixture is concentrated and the crude product is subjected to silica gel flash column chromatography eluting with 75% EtOAc in hexanes to 5% MeOH in DCM to give the title compound (2.12 g, 77.6%) as a pale yellow solid. LC/MS (m/z): 357 (M+H).

Preparation 28

Racemic (cis)-N-[2-Cyanotetrahydropyran-4-yl]-N-cyclopropyl-3-(trifluoromethyl)benzamide

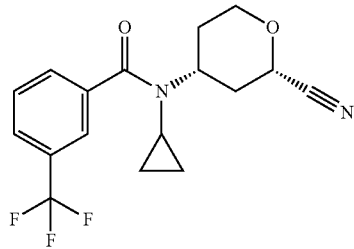 [SMILES: N#C[C@@H]1C[C@H](N(C(=O)c2cccc(C(F)(F)F)c2)C2CC2)CCO1]

Racemic (cis)-4-[cyclopropyl-[3-(trifluoromethyl)benzoyl]amino]tetrahydropyran-2-carboxamide (1.12 g, 6.79 mmol) and pyridine (8 mL) are added together and then thionyl chloride (0.5 mL, 7.0 mmol) is added at 0° C. The mixture is stirred at room temperature for 2 hrs. The mixture is concentrated to provide a residue. The residue is subjected to silica gel flash column chromatography eluting with 0% to 4% MeOH in DCM to give the title compound (0.83 g, 87.4%) as a yellow oil. LC/MS (m/z): 339 (M+H).

Preparation 29

Racemic (cis)-Ethyl-4-[cyclopropyl-[3-(trifluoromethyl)benzoyl]amino]tetrahydropyran-2-carboximidate

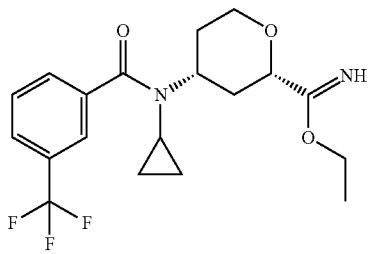 [SMILES: CCOC(=N)[C@@H]1C[C@H](N(C(=O)c2cccc(C(F)(F)F)c2)C2CC2)CCO1]

To a solution of racemic (cis)-N2-[2-cyanotetrahydropyran-4-yl]-N-cyclopropyl-3-(trifluoromethyl)benzamide (0.425 g, 1.19 mmol) in EtOH (3 mL) is added 4 N HCl (4 mL) in EtOH. The reaction mixture is warmed to room temperature and stirred for 1 hr. The volatiles are removed to provide a crude product (1.19 mmol, 100%) as a yellow solid which can be used without further purification. LC/MS (m/z): 385 (M+H).

Preparation 30

Racemic (cis)-N-Cyclopropyl-N-[2-[N-[[3-(cyclopropylmethyl)-5-methyl-imidazole-4-carbonyl]amino]carbamimidoyl]tetrahydropyran-4-yl]-3-(trifluoromethyl)benzamide

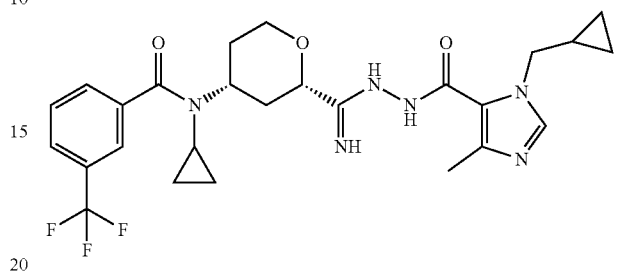

To a solution of racemic (cis)-ethyl-4-[cyclopropyl-[3-(trifluoromethyl)benzoyl]amino]tetrahydropyran-2-carboximidate (1.19 mmol) in acetonitrile (10 mL) are added triethylamine (0.5 mL, 3.57 mmol) and 3-(cyclopropylmethyl)-5-methyl-imidazole-4-carbohydrazide (0.38 g, 1.78 mmol). The mixture is warmed to 50° C. and is stirred overnight. The volatiles are removed to provide a crude product as a yellow solid (0.95 mmol, 80%) which can be used without further purification. LC/MS (m/z): 533 (M+H).

Preparation 31

Cis (chiral)-N-[2-[2-[(1,4-dimethyl-1H-imidazole-5-carbonyl)hydrazine-1-carbonyl]tetrahydro-2H-pyran-4-yl]-N-methyl-3-(trifluoromethoxy)benzamide, Isomer 1

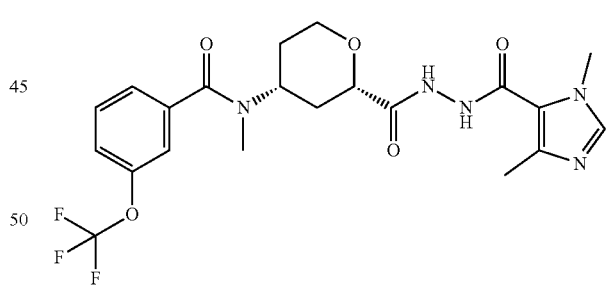

Cis-(chiral)-4-(N-methyl-3-(trifluoromethoxy)benzamido)tetrahydro-2H-pyran-2-carboxylic acid, Isomer 1 (0.287 g, 0.785 mmol) and THF (20 mL) are combined. The mixture is cooled to 0° C. and CDI (0.14 g, 0.864 mmol) is added. The mixture is warmed to room temperature and stirred for 20 min. The reaction mixture is cooled to 0° C. and 3,5-dimethylimidazole-4-carbohydrazide (0.133 g, 0.864 mmol) is added. The mixture is stirred at room temperature overnight. The mixture is concentrated to provide a residue. The residue is subjected to silica gel flash chromatography eluting with 5-10% MeOH in DCM to give the title compound (0.34 g, 85%). LC-MS (m/z): 484 (M+H).

Preparation 32

Cis(chiral)-N-[2-[[[3-(cyclopropylmethyl)-5-methyl-imidazole-4-carbonyl]amino]carbamoyl]tetrahydro-pyran-4-yl]-N-methyl-3-(trifluoromethyl)benzamide, Isomer 1

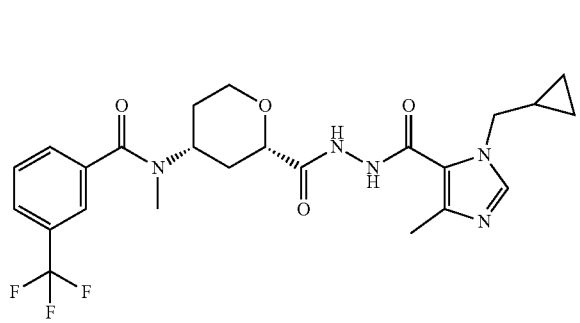 [SMILES: Cc1ncn(CC2CC2)c1C(=O)NNC(=O)[C@@H]1C[C@H](N(C)C(=O)c2cccc(C(F)(F)F)c2)CCO1]

Cis(chiral)-N-[2-[[[3-(cyclopropylmethyl)-5-methyl-imidazole-4-carbonyl]amino]carbamoyl]tetrahydropyran-4-yl]-N-methyl-3-(trifluoromethyl) benzamide, Isomer 1 is prepared essentially as described in Preparation 31. ES/MS (m/z) 508 (M+H).

Preparation 33

Cis-(chiral)-N-(2-(2-(Imidazo[1,2-a]pyridine-3-carbonyl)hydrazine-1-carbonyl)tetrahydro-2H-pyran-4-yl)-N-methyl-3-(trifluoromethyl)benzamide, Isomer 1

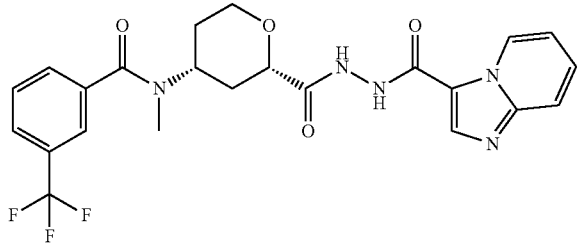 [SMILES: CN(C(=O)c1cccc(C(F)(F)F)c1)[C@@H]1CCO[C@H](C(=O)NNC(=O)c2cnc3ccccn23)C1]

Cis-(chiral)-Methyl-4-[N-methyl-3-(trifluoromethyl)benzamido]tetrahydro-2H-pyran-2-carboxylate, Isomer 1 (1.0 g, 3.0 mmol) and imidazo[1,2-a]pyridine-3-carbohydrazide (0.82 g, 4.4 mmol) are combined in DMF (10 mL). The mixture is stirred to provide a clear solution. Diisopropylethylamine (1.0 mL, 5.7 mmol) is added followed by HATU (2.0 g, 5.2 mmol). The mixture is stirred for 10 hrs. The solvent is removed and the residue is subjected to silica gel flash chromatography eluting with EtOAc/hexanes (1:1) to give the title compound (1.4 g, 95%). LC/MS (m/z): 490 (M+H).

Preparation 34

Cis-(chiral)-N-[2-[2-[(1,4-Dimethyl-1H-imidazole-5-carbonyl)hydrazine-1-carbonyl]tetrahydro-2H-pyran-4-yl]-N-methyl-3-(trifluoromethoxy)benzamide, Isomer 2

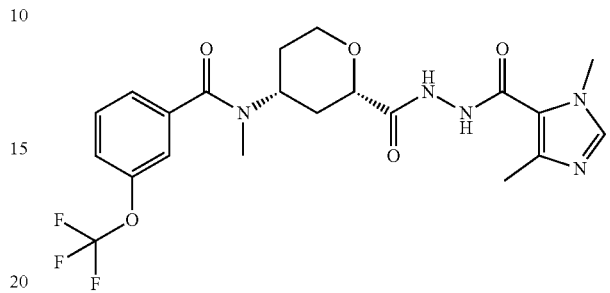

Cis-(chiral)-N-[2-[2-[(1,4-Dimethyl-1H-imidazole-5-carbonyl)hydrazine-1-carbonyl]tetrahydro-2H-pyran-4-yl]-N-methyl-3-(trifluoromethoxy)benzamide, Isomer 2 is prepared essentially as described for Preparation 32.

Preparation 35

Cis-(chiral)-N-[2-[5-(1,4-Dimethyl-1H-imidazol-5-yl)-1,3,4-oxadiazol-2-yl]tetrahydro-2H-pyran-4-yl]-N-methyl-3-(trifluoromethyl)benzamide, Isomer 1

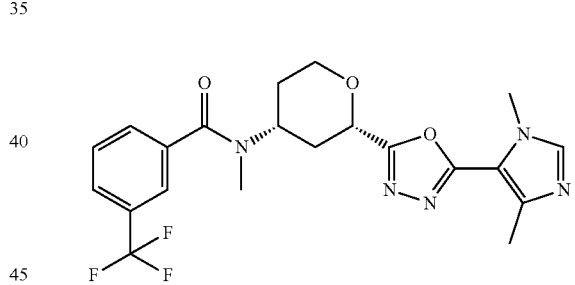

Cis-(chiral)-4-[N-methyl-3-(trifluoromethyl)benzamido]tetrahydro-2H-pyran-2-carboxylic acid, Isomer 1 (3.10 g, 8.59 mmol), 1,4-dimethyl-1H-imidazole-5-carbohydrazide (1.67 g, 9.78 mmol), HATU (3.79 g, 9.78 mmol), N,N-diisopropylethylamine (3.41 mL, 19.6 mmol) are combined in THF (40 mL). The mixture is stirred at room temperature for 45 min Burgess reagent (6.62 g, 26.7 mmol) is added at room temperature and the mixture is stirred at room temperature for 3 hrs. The volatiles are removed in vacuo. Water and EtOAc are added. The mixture is extracted with EtOAc (2×200 mL). The organic extracts are combined, dried over MgSO$_4$, then filtered. The volatiles are removed to provide a residue. The residue is subjected to silica gel flash chromatography eluting with a gradient of 5% to 10% MeOH in DCM to give the product as a white solid (3.15 g, 79.1%). LC/MS (m/z): 450 (M+H).

The following compounds are prepared essentially as described for Preparation 35, starting with the appropriate carboxylic acid. The reaction is stirred for about 3 hrs to overnight.

TABLE 3

| Prep No. | Chemical Name | Structure | ES/MS (m/z) |
|---|---|---|---|
| 36 | Cis-(chiral)-3-Chloro-N-[2-[5-(1,4-dimethyl-1H-imidazol-5-yl)-1,3,4-oxadiazol-2-yl]tetrahydro-2H-pyran-4-yl]-N-methyl-benzamide, Isomer 1 | 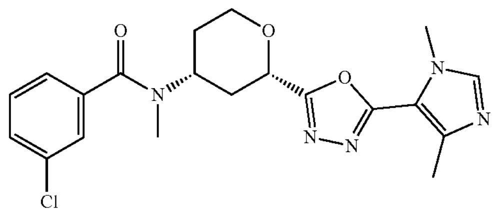 [SMILES: Cc1ncn(C)c1-c1nnc([C@@H]2C[C@H](N(C)C(=O)c3cccc(Cl)c3)CCO2)o1] | 416 |
| 37 | Cis-(chiral)-N-[2-[5-(6,7-Dihydro-5H-pyrrolo[1,2-a]imidazol-3-yl)-1,3,4-oxadiazol-2-yl]tetrahydropyran-4-yl]-N-methyl-3-(trifluoromethyl)benzamide, Isomer 1 | 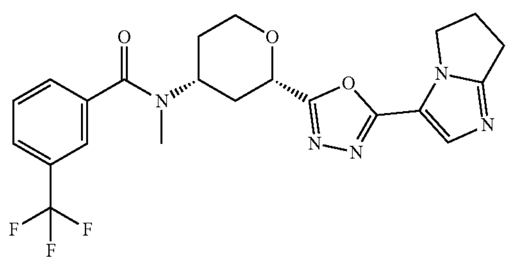 [SMILES: CN(C(=O)c1cccc(C(F)(F)F)c1)[C@@H]1CCO[C@H](c2nnc(-c3cnc4n3CCC4)o2)C1] | 462 |
| 38 | Cis-(chiral)-N-[2-[5-(6,8-Dihydro-5H-imidazo[2,1-c][1,4]oxazin-3-yl)-1,3,4-oxadiazol-2-yl]tetrahydropyran-4-yl]-N-methyl-3-(trifluoromethyl)benzamide, Isomer 1 | 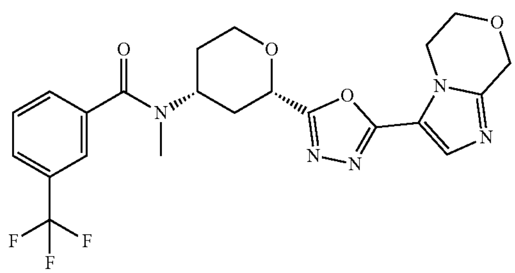 [SMILES: CN(C(=O)c1cccc(C(F)(F)F)c1)[C@@H]1CCO[C@H](c2nnc(-c3cnc4n3CCOC4)o2)C1] | 478 |
| 39 | Cis-(chiral)-N-[2-[5-(3-cyclobutyl-5-methyl-imidazol-4-yl)-1,3,4-oxadiazol-2-yl]tetrahydropyran-4-yl]-N-methyl-3-(trifluoromethyl)benzamide, Isomer 1 | 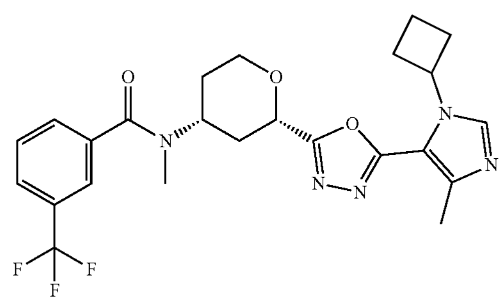 [SMILES: Cc1ncn(C2CCC2)c1-c1nnc([C@@H]2C[C@H](N(C)C(=O)c3cccc(C(F)(F)F)c3)CCO2)o1] | 490 |
| 40[a] | Cis-(chiral)-3-Chloro-N-{2-[5-(imidazo[1,2-a]pyridin-3-yl)-1,3,4-oxadiazol-2-yl]tetrahydro-2H-pyran-4-yl)-N-methylbenzamide, Isomer 1 | 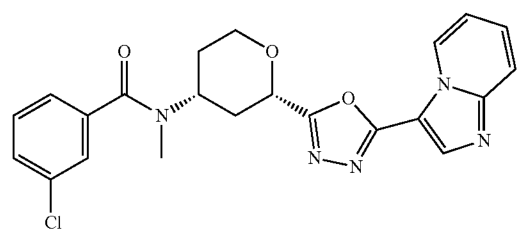 [SMILES: CN(C(=O)c1cccc(Cl)c1)[C@@H]1CCO[C@H](c2nnc(-c3cnc4ccccn34)o2)C1] | 438 |
| 41[a] | Cis-(chiral)-3-Chloro-N-[2-[5-(imidazo[1,2-a]pyridin-3-yl)-1,3,4-oxadiazol-2-yl]tetrahydro-2H-pyran-4-yl}-N-methylbenzamide, Isomer 2 | 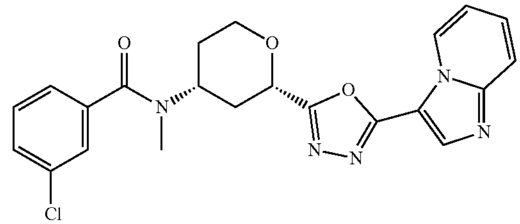 [SMILES: CN(C(=O)c1cccc(Cl)c1)[C@@H]1CCO[C@H](c2nnc(-c3cnc4ccccn34)o2)C1] | 438 |

[a]The reaction is stirred for 10 hrs at room temperature and purified by Chiral Pre-HPLC Instrument: MG II preparative SFC (SFC-1), column: ChiralPak AD-H, 250 × 30 mm I.D, column temperature: 38° C., mobile phase: $CO_2$/isopropanol = 50/50, flow rate: 60 mL/min, back pressure: 100 bar, detection wavelength: 220 nm to give Prep. 40, 100% ee, $R_t$ 5.12 minutes, Prep. 41, 99.2% ee, $R_t$ 3.48 min.

Alternate Preparation 35

Cis-(chiral)-N-[2-[5-(1,4-Dimethyl-1H-imidazol-5-yl)-1,3,4-oxadiazol-2-yl]tetrahydro-2H-pyran-4-yl]-N-methyl-3-(trifluoromethyl)benzamide, Isomer 1

Cis-(chiral)-4-[N-Methyl-3-(trifluoromethyl)benzamido]tetrahydro-2H-pyran-2-carboxylic acid, Isomer 1 (152.2 g, 459.4 mmol), 1,4-dimethyl-1H-imidazole-5-carbohydrazide (85 g, 551 mmol), and HATU (194 g, 510 mmol) are added to THF (2.4 L). N,N-Diisopropylamine (133.7 g, 1.03 mol) is added, and the mixture is stirred at 10-15° C. for 1 hr. Burgess reagent is added (438 g, 1.84 mol), and the mixture is stirred at 10-15° C. for 3 hrs. The volatiles are removed to provide a residue. The residue is combined with material prepared essentially by the same procedure. EtOAc (20 volumes) and water (10 volumes) are added. The mixture is stirred for 30 mins. The aqueous and organic layers are separated. The organic layer is washed with water (3×10 volumes). The volatiles are removed. The material is combined with additional material prepared essentially by the same procedure. The combined material is subjected to silica gel column chromatography eluting with 5% MeOH in DCM to give material that is dissolved in DCM (20 volumes) and washed with water (2×20 volumes). The volatiles are removed to give the title product (701 g).

Preparation 41a

N-{(2S,4R)-2-[4-Benzyl-5-(1,4-dimethyl-1H-imidazol-5-yl)-4H-1,2,4-triazol-3-yl]tetrahydro-2H-pyran-4-yl}-N-methyl-3-(trifluoromethyl)benzamide

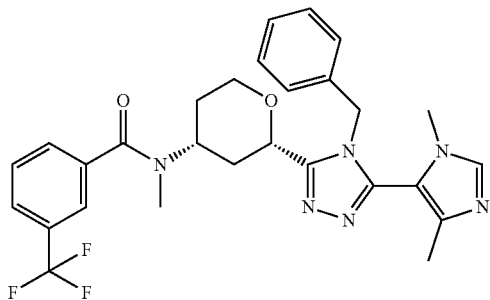 [SMILES: Cc1ncn(C)c1-c1nnc([C@@H]2C[C@H](N(C)C(=O)c3cccc(C(F)(F)F)c3)CCO2)n1Cc1ccccc1]

Cis-(chiral)-N-[2-[5-(1,4-Dimethyl-1H-imidazol-5-yl)-1,3,4-oxadiazol-2-yl]tetrahydro-2H-pyran-4-yl]-N-methyl-3-(trifluoromethyl)benzamide, Isomer 1 (466 g. 1.04 mol), benzylamine (223.6 g, 2.09 mol), 4-toluenesulfonic acid (39.6 g, 218 mmol), and xylene (2.3 L) are combined. The mixture is heated to 120-130° for 21 hrs. The solution is cooled to 50° C. The volatiles are removed. DCM (20 volumes) and water (20 volumes) are added. The mixture is stirred for 30 mins. The organic and aqueous layers are separated. The organic layer is washed with water (20 volumes). The volatiles are removed to provide a residue. The residue is subjected to silica gel chromatography eluting with 5% MeOH in DCM to give the title product (350 g, 62.7%, 94.8% purity).

Preparation 42

Cis-(chiral)-N-[2-[5-(1,4-Dimethyl-1H-imidazol-5-yl)-1,3,4-oxadiazol-2-yl]tetrahydro-2H-pyran-4-yl]-N-methyl-3-(trifluoromethoxy)benzamide, Isomer 1

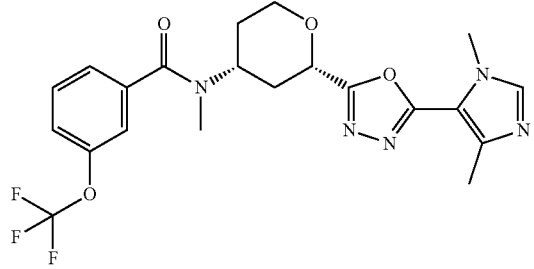 [SMILES: Cc1ncn(C)c1-c1nnc([C@@H]2C[C@H](N(C)C(=O)c3cccc(OC(F)(F)F)c3)CCO2)o1]

Cis (chiral)-N-[2-[2-[(1,4-dimethyl-1H-imidazole-5-carbonyl)hydrazine-1-carbonyl]tetrahydro-2H-pyran-4-yl]-N-methyl-3-(trifluoromethoxy)benzamide, Isomer 1 (0.34 g, 0.668 mmol) and 4 Å molecule sieves are combined in THF (10 mL). Burgess reagent (0.636 g, 2.67 mmol) is added. The mixture is stirred at 80° C. for 5 hrs. The mixture is filtered. The volatiles are removed in vacuo. The residue is subjected to silica gel flash chromatography eluting with 2-8% MeOH in DCM to give the title compound (0.192 g, 59%). LC/MS (m/z): 466 (M+H).

Preparation 43

Cis-(chiral)-N-[2-[5-[3-(Cyclopropylmethyl)-5-methyl-imidazol-4-yl]-1,3,4-oxadiazol-2-yl]tetrahydropyran-4-yl]-N-methyl-3-(trifluoromethyl)benzamide, Isomer 1

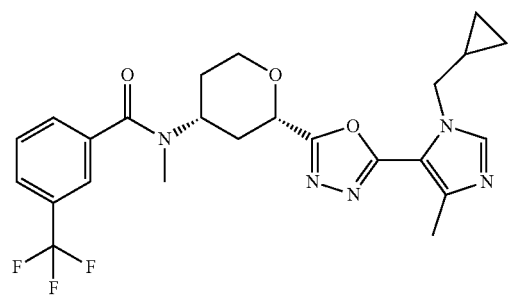 [SMILES: Cc1ncn(CC2CC2)c1-c1nnc([C@@H]2C[C@H](N(C)C(=O)c3cccc(C(F)(F)F)c3)CCO2)o1]

Cis-(chiral)-N-[2-[5-[3-(Cyclopropylmethyl)-5-methyl-imidazol-4-yl]-1,3,4-oxadiazol-2-yl]tetrahydropyran-4-yl]-N-methyl-3-(trifluoromethyl)benzamide, Isomer 1 is prepared essentially as described in Preparation 42. ES/MS (m/z) 490 (M+H).

Preparation 44

Cis-(chiral)-N-[2-[5-(3,5-Dimethylimidazol-4-yl)-1,3,4-oxadiazol-2-yl]tetrahydropyran-4-yl]-N-methyl-3-(trifluoromethoxy)benzamide, Isomer 1

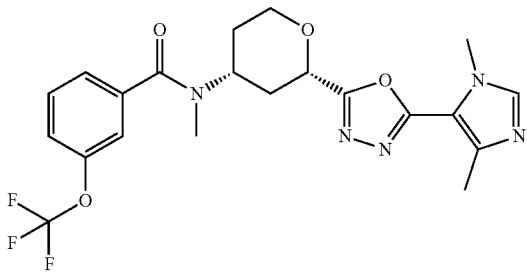 [SMILES: Cc1ncn(C)c1-c1nnc([C@@H]2C[C@H](N(C)C(=O)c3cccc(OC(F)(F)F)c3)CCO2)o1]

Cis-(chiral)-N-[2-[5-(3,5-Dimethylimidazol-4-yl)-1,3,4-oxadiazol-2-yl]tetrahydropyran-4-yl]-N-methyl-3-(trifluoromethoxy)benzamide, Isomer 1 is prepared essentially as described in Preparation 42 with the modification that molecular sieves are not used. ES/MS (m/z) 466 (M+H).

Preparation 45

Cis-(chiral)-N-2-(5-(imidazo[1,2-a]pyridin-3-yl)-1,3,4-oxadiazol-2-yl)tetrahydro-2H-pyran-4-yl)-N-methyl-3-(trifluoromethyl)benzamide, Isomer 1

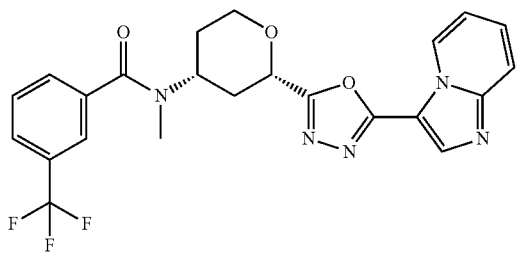 [SMILES: CN(C(=O)c1cccc(C(F)(F)F)c1)[C@@H]1CCO[C@H](c2nnc(-c3cnc4ccccn34)o2)C1]

Cis-(chiral)-N-(2-(2-(Imidazo[1,2-a]pyridine-3-carbonyl)hydrazine-1-carbonyl)tetrahydro-2H-pyran-4-yl)-N-methyl-3-(trifluoromethyl)benzamide, Isomer 1 (1.4 g, 2.9 mmol) is added to THF (50 mL). Burgess reagent (0.30 g, 1.2 mmol) is added. The mixture is stirred for 10 hrs at room temperature. The solvent is removed, and the residue is subjected to silica gel flash chromatography eluting with EtOAc/hexanes (1:1) to give the title compound (1.2 g, 89%). LC/MS (m/z): 472 (M+H).

EXAMPLES

Example 1

Cis-(chiral)-N-[(2-[5-(1,4-Dimethyl-1H-imidazol-5-yl)-4H-1,2,4-triazol-3-yl]tetrahydro-2H-pyran-4-yl]-N-methyl-3-(trifluoromethyl)benzamide, Isomer 1

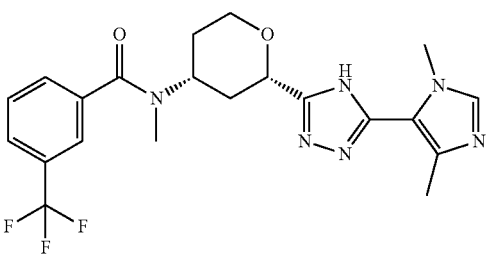 [SMILES: Cc1ncn(C)c1-c1nnc([C@@H]2C[C@H](N(C)C(=O)c3cccc(C(F)(F)F)c3)CCO2)[nH]1]

Cis-(chiral)-N-[2-[5-(3,5-dimethylimidazol-4-yl)-1,3,4-oxadiazol-2-yl]tetrahydropyran-4-yl]-N-methyl-3-(trifluoromethyl)benzamide, Isomer 1 (3.51 g, 7.03 mmol), ammonium acetate (5.42 g, 70.3 mmol), and acetic acid (60 mL) are combined. The mixture is heated at 150° C. under microwave conditions for 5 hrs. The volatiles are removed in vacuo to provide a residue. Saturated $Na_2CO_3$ is added to neutralize the residual acetic acid. The mixture is extracted with DCM (2×300 mL). The organic extracts are combined and dried over $MgSO_4$. The volatiles are removed. The residue is subjected to reverse phase flash chromatography eluting with 12-32% acetonitrile in water with 10 mM $NH_4HCO_3$ to give the title compound as a white solid (689 mg, 21.6%). LC/MS (m/z): 449 (M+H).

The following compounds are prepared essentially as described for Example 1 starting with the appropriate intermediates.

TABLE 4

| Ex. No. | Chemical Name | Structure | ES/MS (m/z) |
|---|---|---|---|
| 2 | Cis-(chiral)-N-[2-[5-(1,4-Dimethyl-1H-imidazol-5-yl)-4H-1,2,4-triazol-3-yl]tetrahydro-2H-pyran-4-yl]-N-methyl-3-(trifluoromethoxy)benzamide, Isomer 1 | 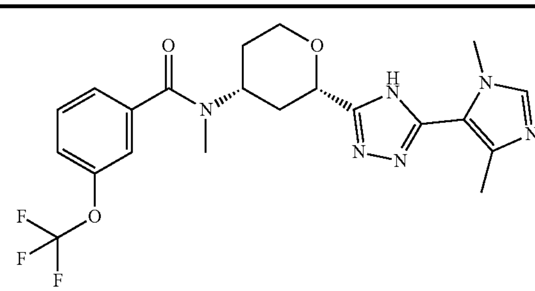 | 465 |

TABLE 4-continued

| Ex. No. | Chemical Name | Structure | ES/MS (m/z) |
|---|---|---|---|
| 3 | Cis-(chiral)-3-Chloro-N-[2-[5-(1,4-dimethyl-1H-imidazol-5-yl)-4H-1,2,4-triazol-3-yl]tetrahydro-2H-pyran-4-yl]-N-methyl-benzamide, Isomer 1 | 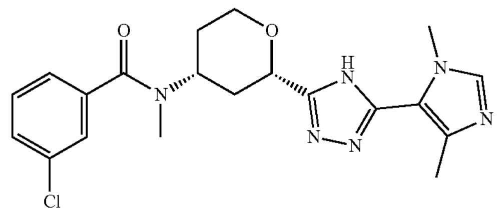 [SMILES: Cc1ncn(C)c1-c1nnc([C@@H]2C[C@H](N(C)C(=O)c3cccc(Cl)c3)CCO2)[nH]1] | 415 |
| 4 | Cis-(chiral)-N-[2-[5-[3-(Cyclopropylmethyl)-5-methyl-imidazol-4-yl]-4H-1,2,4-triazol-3-yl]tetrahydropyran-4-yl]-N-methyl-3-(trifluoromethyl)benzamide, Isomer 1 | 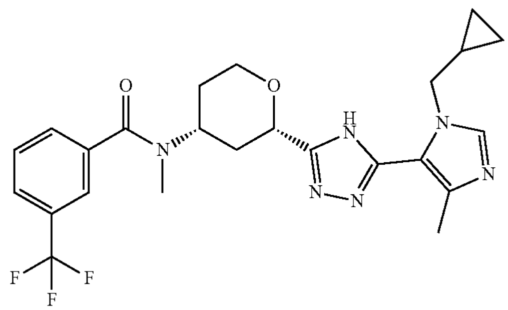 [SMILES: Cc1ncn(CC2CC2)c1-c1nnc([C@@H]2C[C@H](N(C)C(=O)c3cccc(C(F)(F)F)c3)CCO2)[nH]1] | 489 |
| 5 | Cis-(chiral)-N-[2-[5-(6,7-Dihydro-5H-pyrrolo[1,2-a]imidazol-3-yl)-4H-1,2,4-triazol-3-yl]tetrahydropyran-4-yl]-N-methyl-3-(trifluoromethyl)benzamide, Isomer 1 | 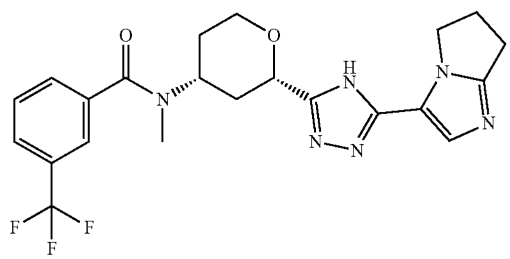 | 461 |
| 6 | Cis-(chiral)-N-[2-[5-(6,8-Dihydro-5H-imidazo[2,1-c][1,4]oxazin-3-yl)-4H-1,2,4-triazol-3-yl]tetrahydropyran-4-yl]-N-methyl-3-(trifluoromethyl)benzamide, Isomer 1 | 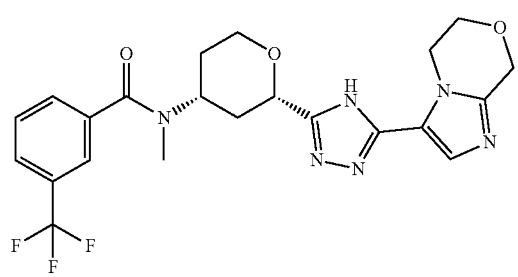 [SMILES: CN(C(=O)c1cccc(C(F)(F)F)c1)[C@@H]1CCO[C@H](c2nnc(-c3cnc4n3CCOC4)[nH]2)C1] | 477 |
| 7 | Cis-(chiral)-N-[2-[5-(3-Cyclobutyl-5-methyl-imidazol-4-yl)-4H-1,2,4-triazol-3-yl]tetrahydropyran-4-yl]-N-methyl-3-(trifluoromethyl)benzamide, Isomer 1 | 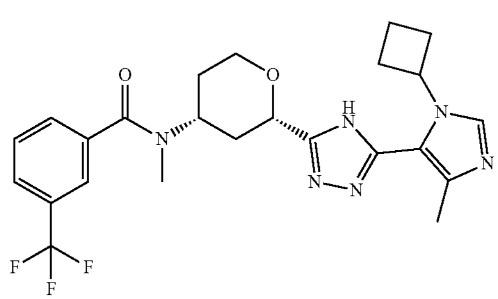 [SMILES: Cc1ncn(C2CCC2)c1-c1nnc([C@@H]2C[C@H](N(C)C(=O)c3cccc(C(F)(F)F)c3)CCO2)[nH]1] | 489 |

TABLE 4-continued

| Ex. No. | Chemical Name | Structure | ES/MS (m/z) |
|---|---|---|---|
| 8[a] | Cis-(chiral)-N-{2-[5-(Imidazo[1,2-a]pyridin-3-yl)-4H-1,2,4-triazol-3-yl]tetrahydro-2H-pyran-4-yl}-N-methyl-3-(trifluoromethyl)benzamide, Isomer 1 | 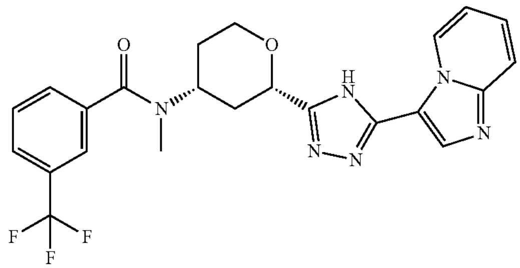 [SMILES: CN(C(=O)c1cccc(C(F)(F)F)c1)[C@@H]1CCO[C@H](c2nnc(-c3cnc4ccccn34)[nH]2)C1] | 471 |
| 9 | Cis-(chiral)-3-Chloro-N-{2-[5-(imidazo[1,2-a]pyridin-3-yl)-4H-1,2,4-triazol-3-yl]tetrahydro-2H-pyran-4-yl}-N-methylbenzamide, Isomer 1 | 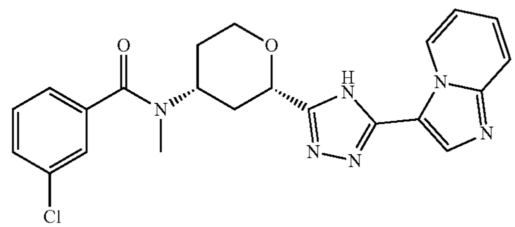 [SMILES: CN(C(=O)c1cccc(Cl)c1)[C@@H]1CCO[C@H](c2nnc(-c3cnc4ccccn34)[nH]2)C1] | 437 |
| 10 | Cis-(chiral)-3-Chloro-N-(2-[5-(imidazo[1,2-a]pyridin-3-yl)-4H-1,2,4-triazol-3-yl]tetrahydro-2H-pyran-4-yl}-N-methylbenzamide, Isomer 2 | 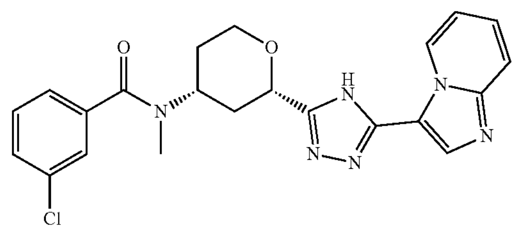 [SMILES: CN(C(=O)c1cccc(Cl)c1)[C@@H]1CCO[C@H](c2nnc(-c3cnc4ccccn34)[nH]2)C1] | 437 |
| 11[b] | Cis-(chiral)-N-{2-[5-(1,4-dimethyl-1H-imidazol-5-yl)-4H-1,2,4-triazol-3-yl]tetrahydro-2H-pyran-4-yl}-N-methyl-3-(trifluoromethoxy)benzamide, Isomer 2 | 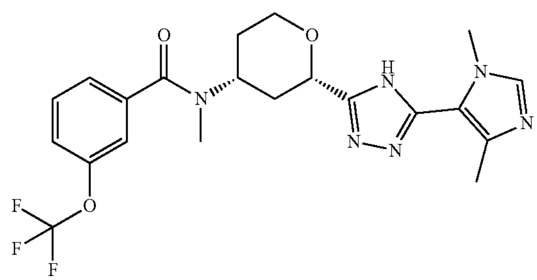 [SMILES: Cc1ncn(C)c1-c1nnc([C@@H]2C[C@H](N(C)C(=O)c3cccc(OC(F)(F)F)c3)CCO2)[nH]1] | 465 |
| 12 | Cis-(chiral)-3-Chloro-N-[2-[5-(1,4-dimethyl-1H-imidazol-5-yl)-4H-1,2,4-triazol-3-yl]tetrahydro-2H-pyran-4-yl]-N-methylbenzamide, Isomer 2 | 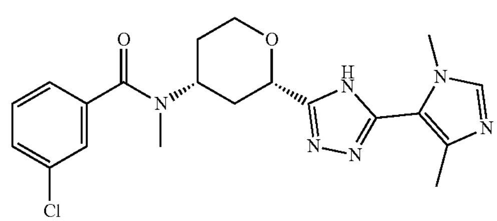 [SMILES: Cc1ncn(C)c1-c1nnc([C@@H]2C[C@H](N(C)C(=O)c3cccc(Cl)c3)CCO2)[nH]1] | 415 |
| 13 | Cis-(chiral)-N-[(2-[5-(1,4-Dimethyl-1H-imidazol-5-yl)-4H-1,2,4-triazol-3-yl]tetrahydro-2H-pyran-4-yl]-N-methyl-3-(trifluoromethyl)benzamide, Isomer 2 | 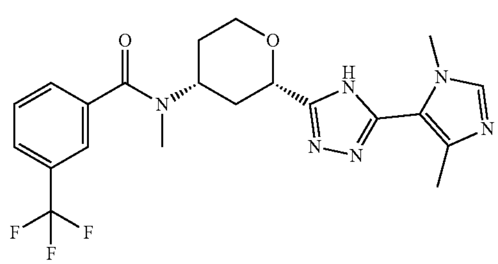 [SMILES: Cc1ncn(C)c1-c1nnc([C@@H]2C[C@H](N(C)C(=O)c3cccc(C(F)(F)F)c3)CCO2)[nH]1] | 449 |

[a]The solvent is removed from the crude product and is purified with silica gel flash chromatography eluting with DCM/MeOH (20:1).
[b]The solvent is removed and the mixture is purified with silica gel chromatography eluting with EtOAc/hexanes and then purified with chiral chromatography, 100% ee, $R_t$ 4.82 min, Instrument: MG II preparative SFC (SFC-1), column: ChiralPak AD-H, 250 × 30 mm I.D, column temperature: 38° C., mobile phase: $CO_2$/MeOH = 75/25, flow rate: 60 mL/min, back pressure: 100 bar, detection wavelength: 220 nm

Alternate Preparation Example 1

Cis-(chiral)-N-[(2-[5-(1,4-Dimethyl-1H-imidazol-5-yl)-4H-1,2,4-triazol-3-yl]tetrahydro-2H-pyran-4-yl]-N-methyl-3-(trifluoromethyl)benzamide, Isomer 1

N-{(2S,4R)-2-[4-Benzyl-5-(1,4-dimethyl-1H-imidazol-5-yl)-4H-1,2,4-triazol-3-yl]tetrahydro-2H-pyran-4-yl}-N-methyl-3-(trifluoromethyl)benzamide (551 g, 1.03 mol) is divided into 5 portions. Each portion (128 g) is added to a hydrogenation bottle with Pd(OH)$_2$/C (12.8 g) and MeOH (6.9 L). The mixture is purged with N$_2$ (3×) and hydrogen (3×). The mixtures are charged with H$_2$ (276-310 kPa) and are heated to 40-45° C. for 20 hrs. Each mixture is filtered. The volatiles are removed. The 5 lots are combined and subjected to silica gel chromatography eluting with 5% MeOH in DCM to give the title compound (374 g, 81.5%, 97.4% purity).

Example 1a

N-{(2S,4R)-2-[5-(1,4-Dimethyl-1H-imidazol-5-yl)-4H-1,2,4-triazol-3-yl]tetrahydro-2H-pyran-4-yl}-N-methyl-3-(trifluoromethyl)benzamide 4-methylbenzenesulfonate Cis-(chiral)-N-[(2-[5-(1,4-Dimethyl-1H-imidazol-5-yl)-4H-1,2,4-triazol-3-yl]tetrahydro-2H-pyran-4-yl]-N-methyl-3-(trifluoromethyl)benzamide, Isomer 1 (350 g, 717 mmol) and acetone (3.5 L) are combined. The mixture is stirred at 100 rpm at 55° C. 4-Methylbenzenesulfonic acid hydrate (155.9 g, 819.6 mmol) is dissolved in acetone (650 mL) and 200 mL of this solution is added over about 30 minutes. A solid precipitates during the addition. The mixture is stirred at 100 rpm at 55° C. The remainder of the 4-methylbenzenesulfonic acid hydrate solution is added over 60 min. The mixture is stirred at 150 rpm for 1 hr at 55° C. The mixture is cooled to 20° C. at 5° C./hr and then stirred at 150 rpm for 20 hrs at 20° C. The mixture is filtered and dried under vacuum at 45° C. for 20 hrs to give the title compound (402 g, 89%, 99.5% purity).

Example 14

Cis-(chiral)-N-Cyclopropyl-N-[2-[5-[3-(cyclopropylmethyl)-5-methyl-imidazol-4-yl]-4H-1,2,4-triazol-3-yl]tetrahydropyran-4-yl]-3-(trifluoromethyl)benzamide, Isomer 2

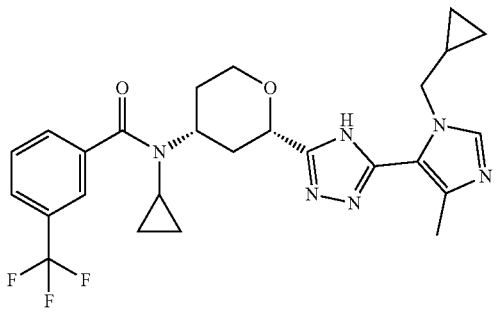 [SMILES: Cc1ncn(CC2CC2)c1-c1nnc([C@@H]2C[C@H](N(C(=O)c3cccc(C(F)(F)F)c3)C3CC3)CCO2)[nH]1]

Racemic (Cis)-N-Cyclopropyl-N-[2-[N-[[3-(cyclopropylmethyl)-5-methyl-imidazole-4-arbonyl]amino] carbamimidoyl]tetrahydropyran-4-yl]-3-(trifluoromethyl)benzamide (0.95 mmol), 4 A molecule sieves (300 mg) and THF (10 mL) are combined. Burgess reagent (0.70 g, 2.86 mmol) is added at room temperature. The mixture is stirred at 80° C. for 4 hrs. The mixture is filtered. The filtrate is collected. The volatiles are removed in vacuo. The residue is subjected to Prep-HPLC eluting with 18-38% acetonitrile (0.1% FA) in water (0.1% FA) to give N-cyclopropyl-N-[(cis)-2-[5-[3-(cyclopropylmethyl)-5-methyl-imidazol-4-yl]-4H-1,2,4-triazol-3-yl]tetrahydropyran-4-yl]-3-(trifluoromethyl)benzamide (64.0 mg, 12.4%) as a white solid. The solid is resolved with chiral chromatography to give the title compound as the second eluting isomer (21.3 mg, 37.7%). LC/MS (m/z): 515 (M+H), 98.2% ee, R$_t$=3.06 minutes, Instrument: MG II preparative SFC (SFC-11), column: ChiralPak AD-H 30*250 mm, 5 µm (Daicel), column temperature: 38° C., mobile phase: CO$_2$/EtOH (0.1% NH$_3$H$_2$O)= 60/40, flow rate: 60 mL/minute, back pressure: 100 bar, detection wavelength: 220 nm, cycle time: ~3 min, sample solution: 55 mg dissolved in MeOH (11 mL), injection volume: 1 mL.

Biological Assays

GPR142 Agonist Effect as Measured by IP-1 Assay

The purpose of this assay is to detect GPR142 agonist effect.

HEK293 cells expressing human GPR142 are maintained in DMEM supplemented with 10% FBS and 800 µg/ml G418 (Geneticin®) at 37° C. and 5% CO$_2$. The cells are plated in 384 well plates at 5000 cells per well and allowed 18 hours for attachment. After addition of compounds at varying concentrations ranging from 30 µM to 1 nM, cells are incubated for 1 hr. IP-1 measurements are performed using an IP-One HTRF® assay kit (Cisbio) according to manufacturer's protocol using assay buffer containing 1×HBSS (+Ca, +Mg), 0.1% BSA, 50 mM LiCl and 20 mM HEPES, pH 7.2. The reaction is stopped by addition of IP1-d2 (IP-1 coupled to an organic HTRF acceptor) followed by cryptate solution (http://www.htrf.com/usa/htrf-chemistry). The plates are incubated at 25° C. for 1 hr. Fluorescence is read in an Envision instrument at 665 nm and 620 nm wavelength. The ratio of 665 nm/620 nm is calculated and converted to IP-1 levels using an IP-1 standard curve. The data is fit to a 4 parameter-fit logistics to determine EC$_{50}$ values.

The compounds of Examples 1-3 herein were tested essentially as described above and exhibited EC$_{50}$ values as shown in the Table below.

TABLE 5

| Example # | hGPR142 IP1 EC$_{50}$ (nM) | Efficacy (%) |
|---|---|---|
| 1 | 43.5 ± 7.9, n = 12 | 109 ± 3, n = 12 |
| 2 | 30.1 ± 4.2, n = 11 | 110 ± 2, n = 11 |
| 3 | 27.2 ± 4.8, n = 7 | 112 ± 3, n = 7 |

Mean ± SEM; SEM = standard error of the mean

These results indicate that the compounds of Formula 1-4 are effective to modulate GPR142.

Intraperitoneal Glucose Tolerance Tests (IPGTT)

IPGTT assay is used to examine the ability of exemplified compounds to activate GPR142 in vivo resulting in antidiabetic efficacy, i.e. reduction in plasma glucose levels. Male C57BL/6 mice (8-10 weeks of age) are fed normal rodent chow diet and water ad libitum. On the night before the study, animals are fasted overnight in clean cages. On the morning of the study, animals are dosed orally with vehicle or compound at the indicated doses 30 minutes prior to the glucose challenge (2 g/kg) by intraperitoneal injection. Blood glucose levels are determined from tail bleeds taken immediately prior to compound dosing (−30 min) and 0, 15, 30, and 60 min after glucose challenge using handheld glucometers. Plasma is isolated from tail bleeds taken at 7 min after glucose challenge and used to determine insulin levels by the Rat/Mouse Insulin Elisa kit (Millipore) or MA6000 Mouse/Rat Insulin Kit (MSD). The blood glucose profile from t=0 to t=60 min is used to calculate an area under the curve (AUC) for each treatment. Percent lowering in glucose AUC is calculated for each treatment group with respect to the AUC of vehicle group. A compound with a reduction in glucose AUC (P<0.05) is considered positive in the assay.

The compounds of Examples 1 and 2 were tested essentially as described above, compared to control, and exhibited $ED_{50}$ and $ED_{80}$ values as shown in the Table below.

TABLE 6

| Example # | $ED_{50}$ (mpk) | $ED_{80}$ (mpk) |
|---|---|---|
| 1 | 0.30 | 1.6 |
| 2 | 0.24 | 1.6 |

The compounds of Examples 1 and 2 are considered positive in the assay and activating GPR142 in vivo resulting in anti-diabetic efficacy.

What is claimed is:

1. A compound of the Formula 1:

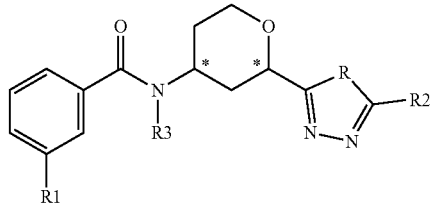

wherein R is —NH or O;
R1 is selected from: —CF$_3$, —OCF$_3$, and halogen;
R2 is selected from:

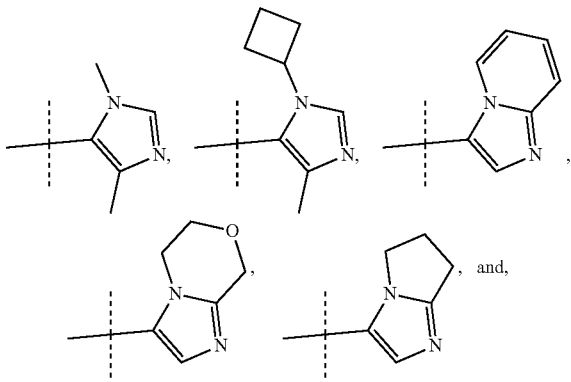

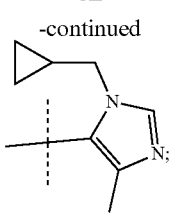

R3 is C$_{1-3}$alkyl or

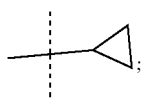

wherein each * designates a chiral center;
or a pharmaceutically acceptable salt thereof.

2. A compound of the Formula 2:

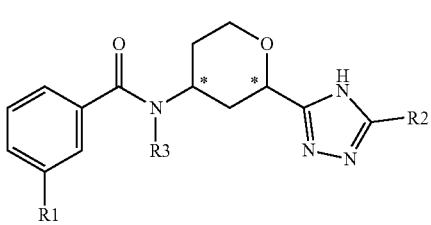

wherein R1 is selected from: —CF$_3$, —OCF$_3$, halogen;
R2 is selected from:

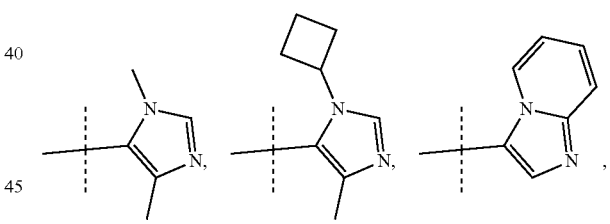

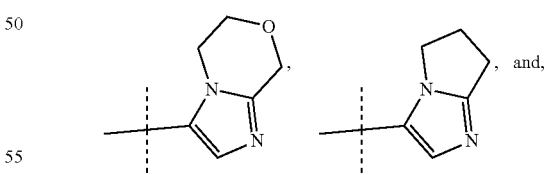

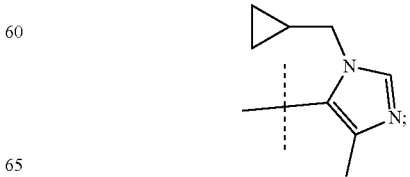

and

R3 is $C_{1-3}$alkyl or

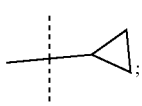

wherein each * designates a chiral center;
or a pharmaceutically acceptable salt thereof.

3. A compound of the Formula 3:

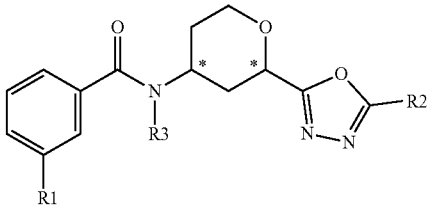

wherein R1 is selected from: —CF$_3$, —OCF$_3$, halogen;
R2 is selected from:

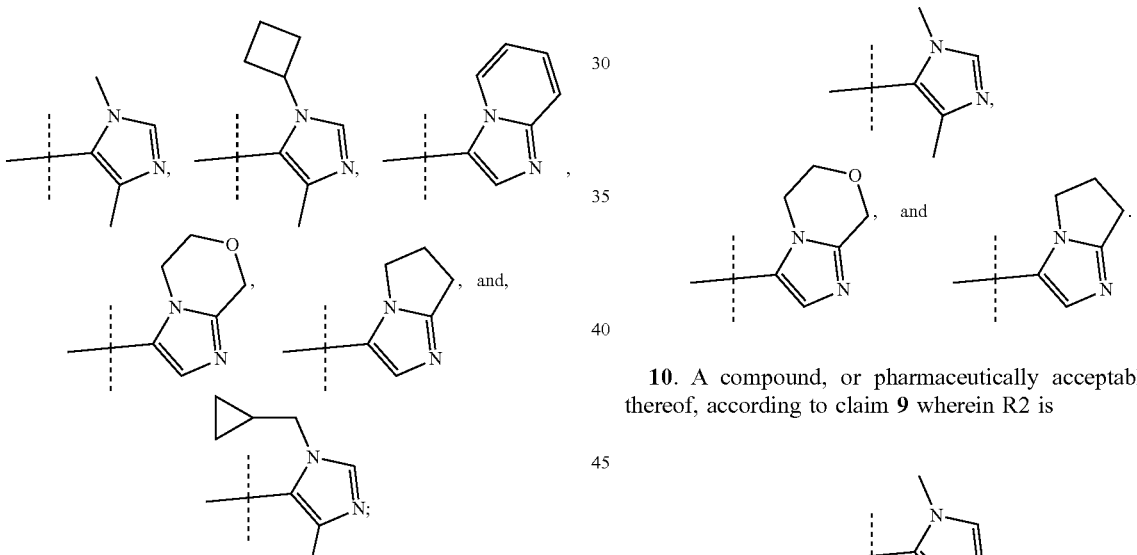

and

R3 is $C_{1-3}$alkyl or

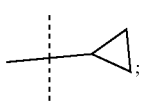

wherein each * designates a chiral center;
or a pharmaceutically acceptable salt thereof.

4. A compound, or a pharmaceutically acceptable salt thereof, according to claim 1 wherein the two chiral centers designated by * are cis relative to one another.

5. A compound, or pharmaceutically acceptable salt thereof, according to claim 1 wherein R1 is selected from: —CF$_3$, —OCF$_3$, and Cl.

6. A compound, or pharmaceutically acceptable salt thereof, according to claim 5 wherein R1 is —CF$_3$ or —OCF$_3$.

7. A compound, or pharmaceutically acceptable salt thereof, according to claim 6 wherein R1 is —CF$_3$.

8. A compound, or pharmaceutically acceptable salt thereof, according to claim 1 wherein R2 is selected from:

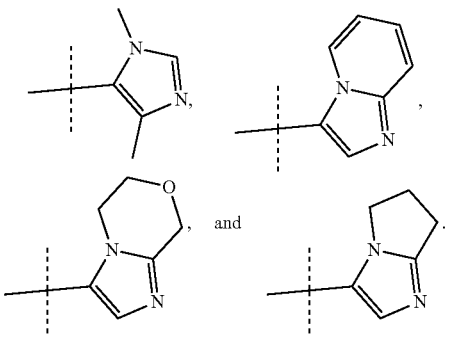

9. A compound, or pharmaceutically acceptable salt thereof, according to claim 8 wherein R2 is selected from:

10. A compound, or pharmaceutically acceptable salt thereof, according to claim 9 wherein R2 is 11. A compound, or pharmaceutically acceptable salt thereof, according to claim 1 wherein R3 is —CH$_3$.

12. A compound, or pharmaceutically acceptable salt thereof, according to claim 1, wherein the compound is selected from:
Cis-(chiral)-N-[(2-[5-(1,4-Dimethyl-1H-imidazol-5-yl)-4H-1,2,4-triazol-3-yl]tetrahydro-2H-pyran-4-yl]-N-methyl-3-(trifluoromethyl)benzamide isomer 1,
Cis-(chiral)-3-Chloro-N-[2-[5-(1,4-dimethyl-1H-imidazol-5-yl)-4H-1,2,4-triazol-3-yl]tetrahydro-2H-pyran-4-yl]-N-methyl-benzamide isomer 1, and
Cis-(chiral)-N-[2-[5-(1,4-Dimethyl-1H-imidazol-5-yl)-4H-1,2,4-triazol-3-yl]tetrahydro-2H-pyran-4-yl]-N-methyl-3-(trifluoromethoxy)benzamide isomer 1.

13. A compound which is

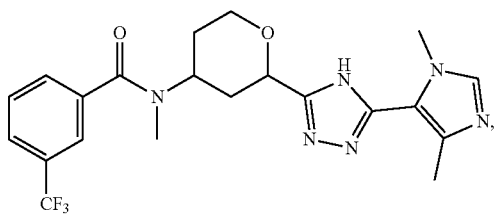 [SMILES: Cc1ncn(C)c1-c1nnc(C2CC(N(C)C(=O)c3cccc(C(F)(F)F)c3)CCO2)[nH]1]

or a pharmaceutically acceptable salt thereof.

14. A compound of the Formula 4

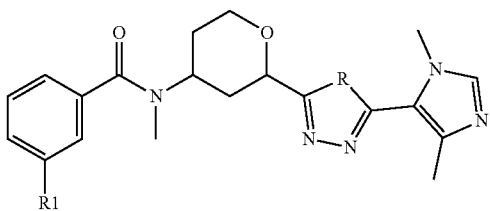

wherein R is selected from the group consisting of O and NH;

R¹ is selected from the group consisting of —CF₃, —OCF₃, and Cl;
or a pharmaceutically acceptable salt thereof.

15. A compound, or pharmaceutically acceptable salt thereof, according to claim 14 wherein R¹ is —CF₃.

16. A compound, or pharmaceutically acceptable salt thereof, according to claim 14 wherein R is NH.

17. A compound, or pharmaceutically acceptable salt thereof, according to claim 14 wherein R is O.

18. A compound, or pharmaceutically acceptable salt thereof, according to claim 17 wherein the orientation of the functional groups at the 2 and 4 position of the tetrahydropyran are in the cis configuration.

19. A pharmaceutical composition comprising a compound according to claim 1, or a pharmaceutically acceptable salt thereof, and at least one of a pharmaceutically acceptable carrier, diluent, or excipient.

20. A method for treating type II diabetes in a mammal in need thereof, comprising administering to the mammal an effective amount of a pharmaceutically acceptable composition according to claim 19.

21. A method for treating type II diabetes in a mammal in need thereof, comprising administering to the mammal an effective amount of a compound, or a pharmaceutically acceptable salt thereof, according to claim 1.

22. A method for treating type II diabetes in a mammal in need thereof, comprising administering to the mammal an effective amount of a pharmaceutically acceptable composition according to claim 14.

* * * * *

UNITED STATES PATENT AND TRADEMARK OFFICE
CERTIFICATE OF CORRECTION

PATENT NO. : 10,196,385 B2
APPLICATION NO. : 15/118295
DATED : February 5, 2019
INVENTOR(S) : Hu et al.

Page 1 of 1

It is certified that error appears in the above-identified patent and that said Letters Patent is hereby corrected as shown below:

In the Claims

Column 41 Line 47: In Claim 1, delete "0;" and insert -- O; --, therefor.

Column 45 Line 28: In Claim 14, delete "0" and insert -- O --, therefor.

Signed and Sealed this
Sixteenth Day of April, 2019

Andrei Iancu
*Director of the United States Patent and Trademark Office*